US007750103B2

(12) United States Patent
Emrick et al.

(10) Patent No.: US 7,750,103 B2
(45) Date of Patent: Jul. 6, 2010

(54) CYCLOOCTENE MONOMERS AND POLYMERS, AND WATER PURIFICATION ARTICLES AND METHODS UTILIZING THEM

(75) Inventors: Todd Shannon Emrick, South Deerfield, MA (US); Kurt Breitenkamp, Northampton, MA (US)

(73) Assignees: The University of Massachusetts, Boston, MA (US); Board of Regents, The University of Texas System, Austin, TX (US)

( * ) Notice: Subject to any disclaimer, the term of this patent is extended or adjusted under 35 U.S.C. 154(b) by 165 days.

(21) Appl. No.: 11/899,869

(22) Filed: Sep. 7, 2007

(65) Prior Publication Data

US 2008/0142454 A1    Jun. 19, 2008

Related U.S. Application Data

(60) Provisional application No. 60/824,987, filed on Sep. 8, 2006.

(51) Int. Cl.
*C08F 12/30* (2006.01)
*C07C 247/10* (2006.01)

(52) U.S. Cl. .............. 526/288; 526/303.1; 526/305; 526/309; 526/277; 526/308; 210/500.36; 552/8

(58) Field of Classification Search ............. 526/288, 526/305, 310, 312, 277, 303.1, 307–309; 552/8; 210/500.36
See application file for complete search history.

(56) References Cited

U.S. PATENT DOCUMENTS

| 4,365,049 | A | * | 12/1982 | Tsunoda et al. | ............. 526/245 |
| 2002/0147282 | A1 | | 10/2002 | Mayes et al. | |
| 2005/0096454 | A1 | * | 5/2005 | Emrick et al. | ............... 528/425 |

OTHER PUBLICATIONS

Breitenkamp and Emrick. Polymer Capsules Prepared by Photo-Induced Crosslinking of Aryl Azide Functionalized Amphiphilic Graft Copolymers at the Oil-Water Interface. Polymeric Materials: Science & Engineering. 2006, 94, pp. 304-305.*
STIC Search, 65 pages.*
Mizutani et al. (Liquid, Phenylazide-End-Capped Copolymers of Caprolactone and Trimethylene Carbonate: Preparation, Photocuring Characteristics, and Surface Layering. Biomacromolecules, 2002, 3, 668-675).*
Binder et al. (Block copolymers derived from photoreactive 2-oxazolines, 1. Synthesis and micellization behavior. Macromol. Chem. Phys. 2000, 201, 949-957).*

(Continued)

*Primary Examiner*—Milton I Cano
*Assistant Examiner*—Brieann R Fink
(74) *Attorney, Agent, or Firm*—Cantor Colburn LLP

(57) ABSTRACT

Azidoaryl-substituted cyclooctene monomers and synthesized and used in the preparation of various copolymers. Among these copolymers are those prepared from ring-opening metathesis polymerization of cyclooctene, polyethylene glycol-substituted cyclooctene, and azidoaryl-substituted cyclooctene. These copolymers are useful in the formation of crosslinked films that reduce fouling of water purification membranes.

16 Claims, 10 Drawing Sheets
(1 of 10 Drawing Sheet(s) Filed in Color)

OTHER PUBLICATIONS

Demonceau et al. (Novel Ruthenium-Based Catalyst Systems for the Ring-Opening Metathesis Polymerization of Low-Strain Cyclic Olefins. Macromolecules, 1997, 11, 3127-3136).*

K. Breitenkamp and T. Emrick, PMSE Preprints (2006), 94, 304-305.

Ravindra Revanur, Bryan McCloskey, Kurt Breitenkamp, Benny D. Freeman, and Todd Emrick, Amphiphilic Graft Copolymers as Antifouling Coatings for Water Purification Membranes, Sep. 2006 ACS Conference.

Ravindra Revanur, Bryan McCloskey, Kurt Breitenkamp, Benny D. Freeman, and Todd Emrick, Reactive Amphiphilic Graft Copolymer Coatings Applied to Poly(vinylidene fluoride) Ultrafiltration Membranes, Revised Manuscript Received Mar. 15, 2007.

R.W. Baker, E.L. Cussler, W. Eykamp, W.J. Koros, R.L. Riley, and H. Strathmann, Eds., Department of Energy: Publication No. DOE/ER/30133-H1, Springfield, VA, 1990, pp. 5(1)-5(53).

L.J. Zeman and A.L. Zydney in Microfiltration and Ultrafiltration Principles and Applications, Marcel Dekker Inc.: N.Y., 1996, pp. 397-446.

G. Belfort, R.H. Davis, and A.L. Zydney, J. Membr. Sci., 1994, vol. 96, p. 1.

Current Opinion Solid State & Mater Sci. 1997, vol. 2, p. 337.

J.H. Lee, H.B. Lee, J.D. Andrade, Prog. Poly. Sci. 1995, vol. 20, p. 1043.

T. Akizawa, K. Kino, S. Koshikawa, Y. Ikeda, A. Kishida, M. Yamashita, K. Imamura, Trans. Am. Soc. Artif. Intern. Organs 1989, vol. 35, p. 333.

M. Ulbricht, H. Matuschewski, A. Oechel, H.G. Hicke, J. Membr. Sci. 1996, vol. 115, p. 31.

M.S. Shoichet, S.R. Winn, S. Athavale, J.M. Harris, F.T. Gentile, Biotechnol. Bioeng. 1994, vol. 43, p. 563.

V. Thom, K. Jankova, M. Ulbricht, J. Kops, G. Jonsson, Macromol. Chem. Phys. 1998, vol. 199, p. 2723.

M.A. Harmer, Langmuir 1991, vol. 7, p. 2010.

M. Huiman, R.H. Davis, C.N. Bowman, Macromolecules 2000, vol. 33, p. 331.

J.F. Hester, P. Benerjee, Y.Y. Won, A. Akthakul, M.H. Acar, A.M. Mayes, Macromolecules 2002, vol. 35, p. 7652.

H. Iwata, M.I. Ivanchenko, Y. Miyaki, J. Appl. Polym. Sci. 1994, vol. 54, p. 125.

R.M. Boom, I.M. Wienk, T. van den Boomgaard, C.A. Smolders, J. Membr. Sci. 1992, vol. 73, p. 277.

J.F. Hester, A.M. Mayes, J. Membr Sci. 2002, vol. 202, p. 119.

M. Scholl, S. Ding, C.W. Lee, R.H. Grubbs, Org. Lett. 1999, vol. 1, p. 953.

J.A. Love, J.P. Morgan, T.M. Trnka, R.H. Grubbs, Agnew. Chem. Int. Ed. 2002, vol. 41, pp. 4035-4037.

K. Breitenkamp, J. Simeone, E. Jin, T. Emrick, Macromolecules 2002, vol. 35, p. 9249.

K. Breitenkamp, T. Emrick, J. Am. Chem. Soc. 2003, vol. 125, p. 12070.

M. Ferrando, A. Rozek, M. Zator, F. Lopez, C.J. Guell, J. Membr. Sci. 2005, vol. 250, p. 283.

D.S. Breslow, In Azides and Nitrenes—Reactivity and Utility, E.V.S. Scriven, Ed. Academic Press: Orland, FL, 1984, pp. 491-517.

J. Brunner, Annu. Rev. Biochem. 1993, vol. 62, p. 483.

* cited by examiner (b) SEM image of top surface of uncoated SterlitechPVDF-UF (a) SEM image of top surface of uncoated Millipore PVDF-UF

US 7,750,103 B2

CYCLOOCTENE MONOMERS AND POLYMERS, AND WATER PURIFICATION ARTICLES AND METHODS UTILIZING THEM

CROSS REFERENCE TO RELATED APPLICATION

This application claims the benefits of U.S. Provisional Patent Application Ser. No. 60/824,987 filed Sep. 8, 2006, which is fully incorporated herein by reference.

STATEMENT REGARDING FEDERALLY SPONSORED RESEARCH & DEVELOPMENT

The U.S. Government has certain rights in this invention pursuant to National Science Foundation Collaborative Research Grant No. NSF-CTS 0553957.

BACKGROUND OF THE INVENTION

Fouling represents a critically important barrier against wider adoption of polymer membranes for many applications, including water purification. See, for example, R. L. Riley, in *Membrane Separation Systems—A Research & Development Needs Assessment*, R. W. Baker, E. L. Cussler, W. Eykamp, W. J. Koros, R. L. Riley, and H. Strathmann, Eds., Department of Energy: Publication number DOE/ER/30133-H1, Springfield, Va., 1990, pages 5(1)-5(53); L. J. Zeman and A. L. Zydney in *Microfiltration and Ultrafiltration Principles and Applications*, Marcel Dekker Inc.: N.Y., 1996, pages 397-446; and G. Belfort, R. H. Davis, and A. L. Zydney, *J. Membr. Sci.*, 1994, volume 96, page 1. Surface and inner-membrane fouling by solutes such as proteins, emulsified oil droplets, and various types of particles leads to considerable loss in flux and selectively over time. See, K. Scott in *Handbook of Industrial Membranes*, 2nd ed., Elsevier: Oxford, 2003. While a number of commodity polymers have been fabricated into useful and commercially viable membranes, new synthetic polymers designed to improve existing membranes are needed to prevent fouling and/or improve separation efficiency, and advance the performance of existing commercial membranes beyond their current state.

The known anti-fouling and surface active properties of polyethylene oxide (PEO; also known as polyethylene glycol (PEG)), are appealing for integration into polymer membranes. See, I. Szleifer, *Current Opinion Solid State & Mater Sci.* 1997, volume 2, page 337; J. H. Lee, H. B. Lee, J. D. Andrade, *Prog. Polym. Sci.* 1995, volume 20, page 1043. However, the water solubility and crystallinity of PEO make it unsuitable for fabrication into robust membranes for aqueous applications. Thus, covalent attachment of PEO to hydrophobic polymers provides a means by which PEO-based polymers can be integrated into membranes with anti-fouling character, yet maintain the integrity of the membrane in an aqueous environment. PEO has been attached covalently to a variety of membrane materials, including cellulose (see, T. Akizawa, K. Kino, S. Koshikawa, Y. Ikada, A. Kishida, M. Yamashita, K. Imamura, *Trans. Am. Soc. Artif. Intern. Organs* 1989, volume 35, page 333), poly(acrylonitrile) (see, M. Ulbricht, H. Matuschewski, A. Oechel, H. G. Hicke, *J. Membr. Sci.* 1996, volume 115, page 31), polyacrylonitrile-co-vinyl chloride) (see, M. S. Shoichet, S. R. Winn, S. Athavale, J. M. Harris, F. T. Gentile, *Biotechnol. Bioeng.* 1994, volume 43, page 563), polysulfone (see, V. Thom, K. Jankova, M. Ulbricht, J. Kops, G. Jonsson, *Macromol. Chem. Phys.* 1998, volume 199, page 2723; M. A. Harmer, *Langmuir* 1991, volume 7, page 2010), and polypropylene and cellulose acetate (see, M. Huiman, R. H. Davis, C. N. Bowman, *Macromolecules* 2000, volume 33, page 331). Such "PEGylated" membranes typically show considerably different properties from the non-PEGylated versions, especially with respect to reduced fouling, and permeability/selectivity characteristics. See, V. Thom, K. Jankova, M. Ulbricht, J. Kops, G. Jonsson, *Macromol. Chem. Phys.* 1998, volume 199, page 2723; J. F. Hester, A. M. Mayes, *J. Membr. Sci.* 2002, volume 202, page 119; J. F. Hester, P. Benerjee, Y. Y. Won, A. Akthakul, M. H. Acar, A. M. Mayes, Macromolecules 2002, volume 35, page 7652; H. Iwata, M. I. Ivanchenko, Y. Miyaki, *J. Appl. Polym. Sci.* 1994, volume 54, page 125. For polysulfone ultrafiltration (UF) membranes, ultraviolet light-induced reactions of PEG derivatives have been used for membrane surface modification. See, V. Thom, K. Jankova, M. Ulbricht, J. Kops, G. Jonsson, *Macromol. Chem. Phys.* 1998, volume 199, page 2723; M. A. Harmer, *Langmuir* 1991, volume 7, page 2010. In these examples, the ester linkage chosen to connect PEG to the underlying membrane is convenient synthetically, but ultimately not ideally suited for water purification applications due to the hydrolytic instability of esters. Composite membranes prepared from polymer blends, such as polyether sulfone/poly(vinylpyrrolidone) (see, R. M., Boom, I. M. Wienk, T. van den Boomgaard, C. A. Smolders, *J. Membr. Sci.* 1992, volume 73, page 277), and poly(vinylidene fluoride) (PVDF)/PVDF-PEGylated PMMA (see, J. F. Hester, A. M. Mayes, *J. Membr. Sci.* 2002, volume 202, page 119; J. F. Hester, P. Benerjee, Y. Y. Won, A. Akthakul, M. H. Acar, A. M. Mayes, *Macromolecules* 2002, volume 35, page 7652), also provide examples of materials that exhibit reduced fouling relative to conventional commercial membranes. However, potential disadvantages of the blending approach include leaching of the anti-fouling additive over time, inferior physical and mechanical properties of the blended material compared to a homogeneous polymer, and the need for polymer blending steps in the membrane fabrication process.

There remains a need for water purification membranes that are hydrolytically stable and exhibit improved resistance to fouling.

BRIEF DESCRIPTION OF THE INVENTION

One embodiments is an azidoaryl-substituted cyclooctene having the structure

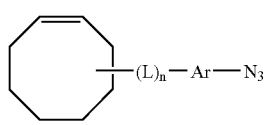

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group.

Another embodiment is a copolymer that is the product of ring-opening metathesis polymerization of monomers comprising an azidoaryl-substituted cyclooctene having the structure

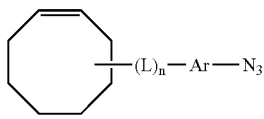

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group.

Another embodiment is a copolymer that is the product of ring-opening metathesis polymerization of monomers comprising 4-azido-N-4-cycloocten-1-yl-benzamide.

Another embodiment is a copolymer that is the product of addition polymerization of monomers comprising an azidoaryl-substituted cyclooctene having the structure

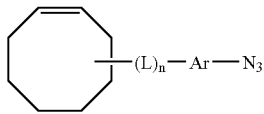

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group.

Another embodiment is a crosslinked copolymer that is the product of photochemically crosslinking a copolymer that is the product of a process comprising polymerizing monomers comprising an azidoaryl-substituted cyclooctene having the structure

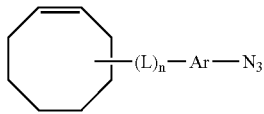

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group.

Another embodiment is a process of forming a crosslinked copolymer film, comprising: forming a film comprising a copolymer that is the product of polymerization of monomers comprising an azidoaryl-substituted cyclooctene; and exposing the film to radiation effective to photolyze the azido group and thereby crosslink the copolymer film.

Another embodiment is a water purification membrane comprising a crosslinked polymer film prepared by a process, comprising: forming a film comprising a copolymer that is the product of polymerization of monomers comprising an azidoaryl-substituted cyclooctene; and exposing the film to radiation effective to photolyze the azido group and thereby crosslink the copolymer film.

Another embodiment is a method of purifying water, comprising: passing water through a membrane comprising a crosslinked copolymer comprising repeating units derived from monomers comprising 4-azido-N-4-cycloocten-1-yl-benzamide, cyclooctene, and an alpha-4-cycloocten-1-yl-omega-hydroxy-poly(oxy-1,2-ethanediyl).

Another embodiment is a method of reducing fouling of a water purification membrane, comprising covalently binding to a water purification membrane a layer comprising a crosslinked copolymer comprising repeating units derived from monomers comprising 4-azido-N-4-cycloocten-1-yl-benzamide, cyclooctene, and an alpha-4-cycloocten-1-yl-omega-hydroxy-poly(oxy-1,2-ethanediyl).

Another embodiment is a method of reducing fouling of a surface, comprising covalently binding to the surface a layer comprising a crosslinked copolymer comprising repeating units derived from monomers comprising 4-azido-N-4-cycloocten-1-yl-benzamide, cyclooctene, and an alpha-4-cycloocten-1-yl-omega-hydroxy-poly(oxy-1,2-ethanediyl).

These and other embodiments, including crosslinked copolymer films prepared by various methods, are described in detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

DETAILED DESCRIPTION OF THE INVENTION

Figure 1:
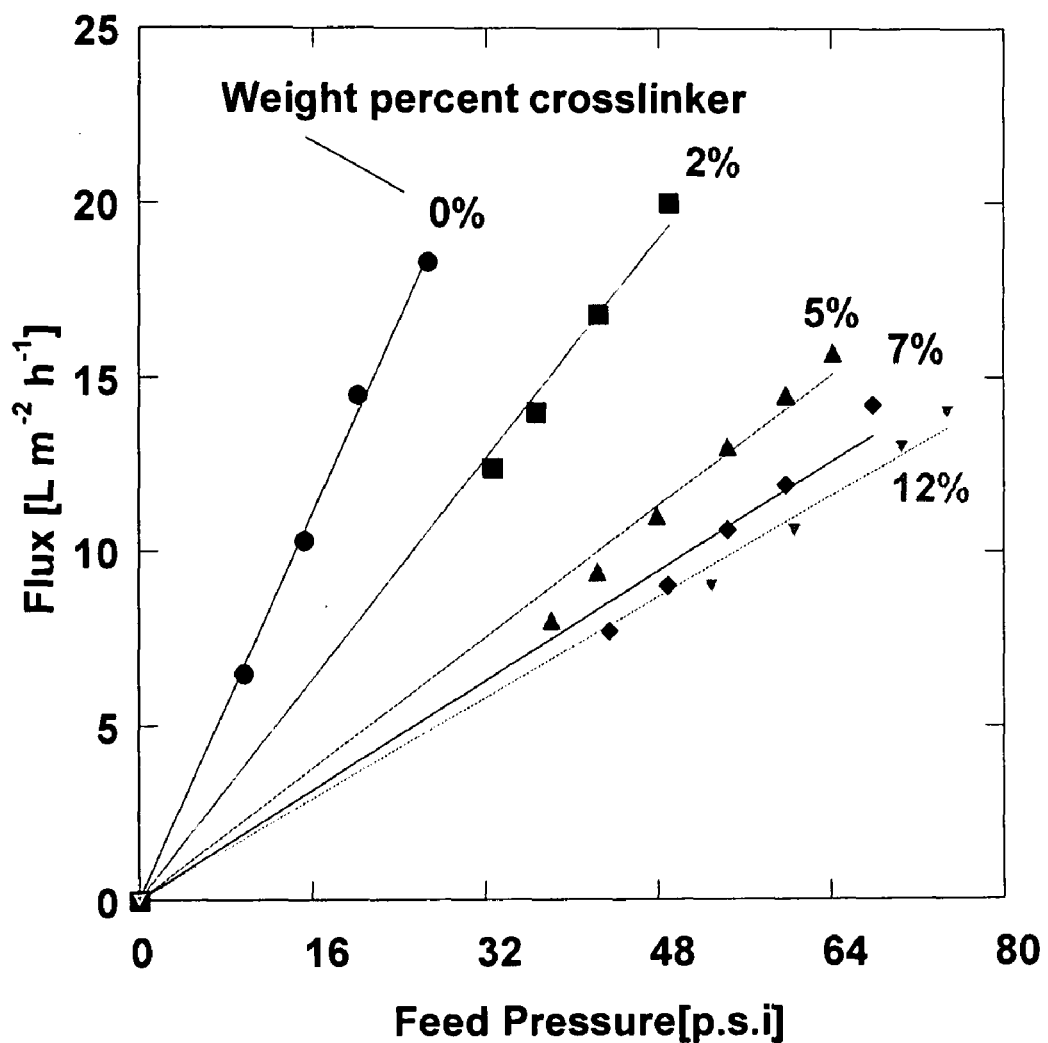
FIG. 1 is a plot of water flux in a dead-end flow setup as a function of pressure and extent of crosslinking for films of a copolymer of cyclooctene and two PEGylated cyclooctenes.

The present inventors, while conducting research on anti-fouling coatings for water purification membranes, prepared and tested polyolefin-graft-PEG amphiphilic graft copolymers. However, it was difficult to prepare anti-fouling coatings from these copolymers that were physically robust and also adhered to the water purification membrane to which they were applied. Previously described methods of chemically crosslinking the coatings did not substantially improve their adhesion to the membranes. In an attempt to solve this problem, the inventors prepared and incorporated into the copolymers an azidoaryl-substituted cyclooctene monomer. The azidoaryl group allows these copolymers to be photochemically crosslinked in a way that both improves their physical robustness and substantially improves their adhesion to the commercial membranes as underlying substrates. Coatings prepared from the copolymers have now been demonstrated to be effective at reducing fouling of water purification membranes and in some cases improving the permeance of such membranes as a result of preventing fouling. This water purification application is just one potential use of the azidoaryl-substituted cyclooctene monomers. They can also be used to prepare a variety of addition copolymers and ring-opening metathesis copolymers that are readily photochemically crosslinked.

Thus, one embodiment is an azidoaryl-substituted cyclooctene having the structure

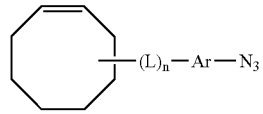

wherein n is 0 or 1; wherein L is selected from —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a divalent C$_6$-C$_{18}$ arylene group. As used herein, the term "hydrocarbyl", whether used by itself, or as a prefix, suffix, or fragment of another term, refers to a residue that contains only carbon and hydrogen. The residue may be aliphatic or aromatic, straight-chain, cyclic, bicyclic, branched, saturated, or unsaturated. It may also contain combinations of aliphatic, aromatic, straight chain, cyclic, bicyclic, branched, saturated, and unsaturated hydrocarbon moieties. The hydrocarbyl residue, when so stated however, may contain heteroatoms over and above the carbon and hydrogen members of the substituent residue. Thus, when specifically noted as containing such heteroatoms, the hydrocarbyl residue may also contain one or more carbonyl groups, amino groups, hydroxyl groups, or the like, or it may contain heteroatoms within the backbone of the hydrocarbyl residue. While not wishing to be bound by any particular theory, the present inventors believe that the use of an azidoaryl group allows photochemical activation of the azido group to form a highly reactive nitrene intermediate, which reacts to crosslink the polycyclooctene copolymer into which it is incorporated. It should be noted that efficient crosslinking as a result of photochemical generation and reactivity of a nitrene intermediate would not occur if the azido group were directly attached to the cyclooctene nucleus or part of an aliphatic pendant group. In contrast to previously described approaches, the azidoaryl group is linked to the cyclooctene nucleus by a hydrolytically stable link: either a direct bond between the cyclooctene and the aryl moiety of the azidoaryl group (n=0), or by a hydrolytically stable linkage selected from —O—, —N(R$^1$)C(=O)—, —C(=O)N(R$^1$)—, —N(R$^1$)S(=O)$_2$—, and —S(=O)$_2$N(R$^1$)— (n=1). It will be understood that the divalent linkages —N(R$^1$)C(=O)—, —C(=O)N(R$^1$)—, —N(R$^1$)S(=O)$_2$—, and —S(=O)$_2$N(R$^1$)— are written such that the left point of attachment is a bond to the cyclooctene and the right point of attachment is a bond to the azidoaryl group. For example, when n is 1 and L is —N(H)C(=O)—, the azidoaryl-substituted cyclooctene has the structure

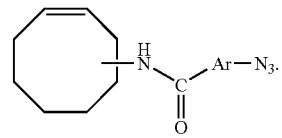

Suitable C$_6$-C$_{18}$ arylene groups, Ar, include, for example, divalent groups having any of the following structures

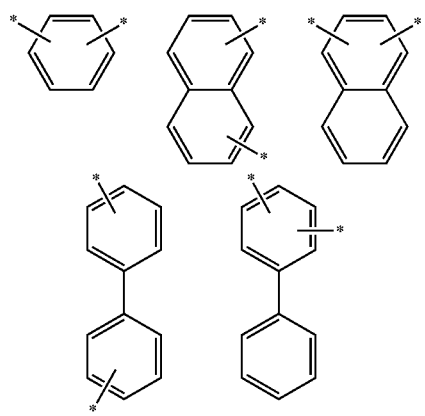

In some embodiments, n is 1, L is —N(H)C(=O)—, and Ar is 1,3-phenylene or 1,4-phenylene. In some embodiments, the azidoaryl-substituted cyclooctene is designated 4-azido-N-4-cycloocten-1-yl-benzamide and has the structure

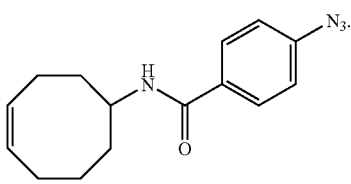

In the generic azidoaryl-substituted cyclooctene structure above, when L is —N(R$^1$)C(=O)—, the L linkage may be formed by reacting a 5-aminocyclooctene with an azidoaryl acid chloride. When L is —C(=O)N(R$^1$)—, the L linkage may be formed, for example by reacting a carboxy-substituted cyclooctene with an amino-substituted aryl azide. When L is —N(R$^1$)S(=O)$_2$—, the L linkage may be formed by reacting a 5-aminocyclooctene with an azidoaryl sulfonyl chloride. When L is —S(=O)$_2$N(R$^1$)—, the L linkage may be formed by reaction of a sulfonyl chloride-substituted cyclooctene with an amino-substituted aryl azide.

The azidoaryl-substituted cyclooctene may be used to form a homopolymer or copolymer via ring-opening metathesis polymerization (ROMP). Thus, one embodiment is a copolymer that is the product of ring-opening metathesis polymerization of monomers comprising an azidoaryl-substituted cyclooctene having the structure

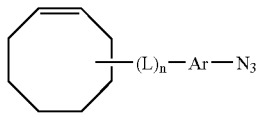

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group. In some embodiments, n is 1, L is —N(H)C(=O)—, and Ar is 1,3-phenylene or 1,4-phenylene. In some embodiments, the azidoaryl-substituted cyclooctene is 4-azido-N-4-cycloocten-1-yl-benzamide. In some embodiments, the monomers used to prepare the ring-opening metathesis derived polymer may include cyclooctene, an azidoaryl-substituted cyclooctene such as 4-azido-N-4-cycloocten-1-yl-benzamide, a polyethylene glycol-substituted cyclooctene such as alpha-4-cyclooctene-1-yl-omega-hydroxy-poly(oxy-1,2-ethanediyl), a phosphorylcholine-substituted cyclooctene (as described below), or a combination thereof.

In some embodiments particularly suitable for use in forming anti-fouling coatings for water purification membranes, the monomers used in ring-opening metathesis polymerization may comprise an alpha-4-cyclooctene-1-yl-omega-hydroxy-poly(oxy-1,2-ethanediyl) comprising about 10 to about 500 oxy-1,2-ethanediyl units. Within this range, the number of oxy-1,2-ethanediyl units (oxyethylene units) may be at least about 20. Also within this range, the number of oxy-1,2-ethanediyl units (oxyethylene units) may be up to about 200, or up to about 100. In some embodiments where the monomers comprise an alpha-4-cyclooctene-1-yl-omega-hydroxy-poly(oxy-1,2-ethanediyl), the copolymer as a whole may comprise about 70 to about 90 weight percent of oxy-1,2-ethanediyl units.

In some embodiments, the monomers used in ring-opening metathesis polymerization may comprise about 10 to about 30 weight percent of 4-azido-N-4-cycloocten-1-yl-benzamide, about 50 to about 70 weight percent of cyclooctene, and about 10 to about 30 weight percent of the alpha-4-cyclooctene-1-yl-omega-hydroxy-poly(oxy-1,2-ethanediyl). Within the above range, the 4-azido-N-4-cyclooctene-1-yl-benzamide amount may be at least about 15 weight percent, or up to about 25 weight percent. Within the above range, the cyclooctene amount may be at least about 55 weight percent, or up to about 65 weight percent. Within the above range, the alpha-4-cyclooctene-1-yl-omega-hydroxy-poly(oxy-1,2-ethanediyl) amount may be at least about 15 weight percent, or up to about 25 weight percent.

In some embodiments particularly suitable for use in forming anti-fouling coatings for water purification membranes, the monomers used in ring-opening metathesis polymerization may comprise a phosphorylcholine-substituted cyclooctene. The phosphorylcholine-substituted cyclooctene may be prepared, for example, as depicted in Schemes 1 and 2 by sequential reaction of a cyclooctene alcohol with ethylene chlorophosphate and a trialkylamine NR$^2_3$ where each occurrence of R$^2$ is C$_1$-C$_6$ alkyl. In some embodiments, the trialkylamine is trimethylamine.

Scheme 1

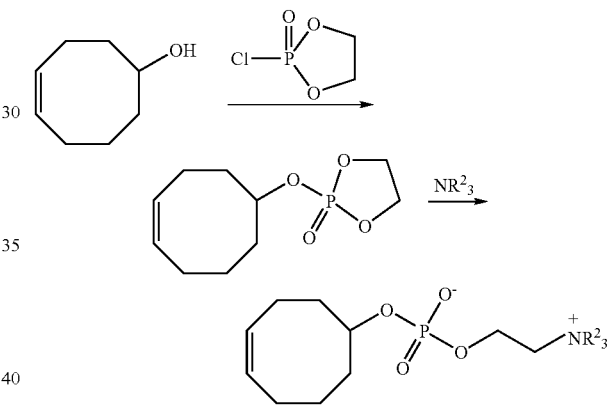

Scheme 2

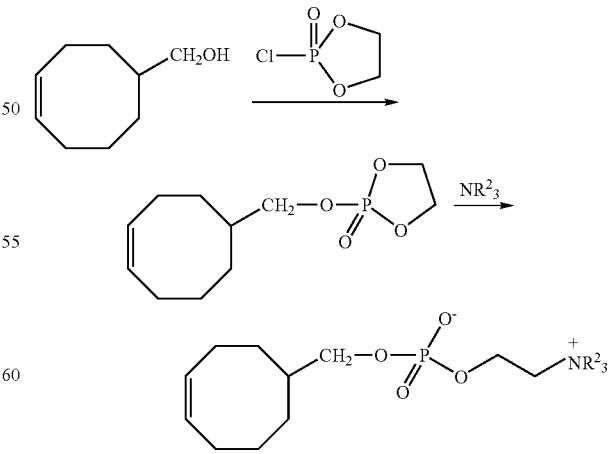

In addition to being used in ring-opening metathesis polymerization, the azidoaryl-substituted cyclooctene may be used in addition polymerization to form photochemically crosslinkable homopolymers and copolymers. Thus, one embodiment is a copolymer that is the product of addition polymerization of monomers comprising an azidoaryl-substituted cyclooctene having the structure

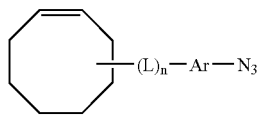

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group. In some embodiments, n is 1, L is —N(H)C(=O)—, and Ar is 1,3-phenylene or 1,4-phenylene. In some embodiments, the azidoaryl-substituted cyclooctene is 4-azido-N-4-cycloocten-1-yl-benzamide. Monomers suitable for addition copolymerization with the azidoaryl-substituted cyclooctene include, for example, C$_2$-C$_{18}$ alkenes (such as ethylene, propylene, butylenes, 4-methyl-1-pentene, 1-hexene, 1-octene, and cyclooctene), C$_4$-C$_{12}$ conjugated dienes (such as butadiene and isoprene), C$_5$-C$_{18}$ nonconjugated dienes (such as 5-ethylidene-2-norbornene, dicyclopentadiene, 1,4-pentadiene, 1,4-hexadiene, 1,5-hexadiene, 1,6-heptadiene, 4-methyl-1,4-hexadiene, 5-methyl-1,4-hexadiene, 1,7-octadiene, 1,8-nonadiene, 7-methyl-1,6-octadiene, 1,9-decadiene, 5-vinyl-2-norbornene and 2,5-norbornadiene), C$_8$-C$_{18}$ alkenyl aromatic compounds (such as styrene, alpha-methylstyrene, 2-methylstyrene, 3-methylstyrene, 4-methylstyrene, 3-t-butylstyrene, and 4-t-butylstyrene), C$_4$-C$_{12}$ alkenyl alkanoates (such as vinyl acetate, vinyl propionate, allyl acetate, and allyl propionate), C$_4$-C$_{12}$ alkyl (meth)acrylates (such as methyl acrylate, methyl methacrylate, ethyl acrylate, ethyl methacrylate, butyl acrylate, and butyl methacrylate), and mixtures thereof. It will be understood that the term "(meth)acrylate" includes "acrylate" and "methacrylate".

Any of the above-described polymers comprising units derived from an azidoaryl-substituted cyclooctene—including ring-opening metathesis polymers and addition polymers—may be photochemically crosslinked. Thus, one embodiment is a crosslinked copolymer that is the product of photochemically crosslinking a copolymer that is the product of a process comprising polymerizing monomers comprising an azidoaryl-substituted cyclooctene having the structure

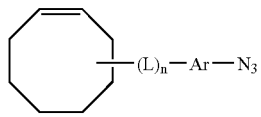

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group.

One embodiment is a process of forming a crosslinked copolymer film, comprising: forming a film comprising a copolymer that is the product of polymerization (including addition polymerization and ring-opening metathesis polymerization) of monomers comprising an azidoaryl-substituted cyclooctene; and exposing the film to radiation effective to photolyze the azido group and thereby crosslink the copolymer film. Radiation effective to photolyze the azido group includes, for example, ultraviolet light.

Crosslinked copolymer films useful as anti-fouling coatings for water purification membranes include those having a thickness of about 100 nanometers to about 1 micrometer. Within this range, the thickness may be at least about 200 nanometers, or at least about 400 nanometers. Also within this range, the thickness may be up to about 800 nanometers, or up to about 600 nanometers.

One embodiment is a water purification membrane comprising the crosslinked polymer film as an anti-fouling coating. In addition to the crosslinked copolymer film, the water purification membrane may include a membrane comprising a polymer such as, for example, a poly(vinylidene fluoride), a polyamide, or a polysulfone. The membrane may be a microfiltration (MF) membrane, an ultrafiltration (UF) membrane, a nanofiltration (NF) membrane, or a reverse osmosis (RO) membrane. The crosslinked copolymer film forms an anti-fouling coating on (that is, in direct contact with) the water purification membrane. In some embodiments, the crosslinked polymer film is subjected to conditions under which it can bond covalently to an underlying membrane support. Suitable methods for forming an anti-fouling coating include coating the uncrosslinked polymer on the membrane using a technique such as dip coating, solution casting, drop casting, spin coating, and spray coating; drying the coating; and crosslinking the coating by exposure to radiation.

One embodiment is a method of purifying water, comprising: passing water through a membrane comprising a crosslinked copolymer comprising repeating units derived from monomers comprising 4-azido-N-4-cycloocten-1-yl-benzamide, cyclooctene, and an alpha-4-cycloocten-1-yl-omega-hydroxy-poly(oxy-1,2-ethanediyl).

Another embodiment is a method of reducing fouling of a water purification membrane, comprising covalently binding to a water purification membrane a layer comprising a crosslinked copolymer comprising repeating units derived from monomers comprising 4-azido-N-4-cycloocten-1-yl-benzamide, cyclooctene, and an alpha-4-cycloocten-1-yl-omega-hydroxy-poly(oxy-1,2-ethanediyl).

The copolymers are useful not only for use in membranes, but also for use to prevent fouling of a variety of hydrophobic surfaces, including solid (nonporous) surfaces. Thus, another embodiment is a method of reducing fouling of a surface, particularly a hydrophobic surface, comprising covalently binding to the surface a layer comprising a crosslinked copolymer comprising repeating units derived from monomers comprising 4-azido-N-4-cycloocten-1-yl-benzamide, cyclooctene, and an alpha-4-cycloocten-1-yl-omega-hydroxy-poly(oxy-1,2-ethanediyl).

While the invention has been described in terms of cyclooctenes and their polymers, it will be understood that other cyclic olefin monomers, such as norbornenes and dicyclopentadienes, can be used in place of or in addition to the cyclooctenes described herein.

The invention is further illustrated by the following non-limiting examples.

Examples 1-3

These examples describe the preparation of PEGylated cyclooctene macromonomers. The PEGylated cyclooctene macromonomers were prepared in a three-step process, as illustrated in Scheme 3. In the first step, the alkoxide of 5-hydroxycyclooctene was formed by reaction with potassium napthalenide. In the second step, the alkoxide of 5-hydroxycyclooctene was used to initiate anionic polymerization of ethylene oxide. In the third step, water was added to terminate the anionic polymerization of ethylene oxide and yield the PEGylated cyclooctene macromonomer. The degree of polymerization of ethylene oxide was varied by changing the number of equivalents of ethylene oxide, m, to provide PEGylated cyclooctene macromonomers 7, 8, and 11 having the structure shown below where the number of ethylene oxide repeat units m was approximately 25, 50, and 100, respectively.

Scheme 3

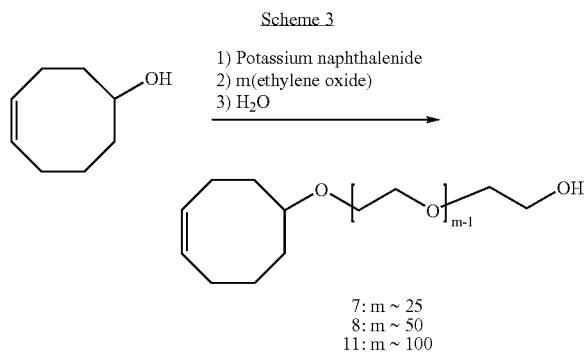

7: m ~ 25
8: m ~ 50
11: m ~ 100

A representative synthetic procedure is as follows. Into a flame dried air-free flask under $N_2$ atmosphere was introduced a tetrahydrofuran (THF) solution of 5-hydroxycyclooctene (1.0 moles per liter, 3.5 milliliters), followed by dry THF (150 milliliters). The solution was titrated with a THF solution of potassium napthalenide (0.2 moles per liter), until a slight green end-point was observed (about 35.0 milliliters). This green solution was stirred for 30 minutes at room temperature, then cooled using an ice/water bath. Ethylene oxide (15.0 milliliters, 340.6 millimoles) was condensed at −78° C. using a stainless steel gas transfer manifold, then slowly warmed to room temperature as it transferred into the cyclooctene alkoxide solution under static vacuum. The reaction mixture was pressurized with argon, sealed, and allowed to stir at room temperature for 16 hours. The solution was concentrated and the macromonomer was purified by column chromatography over silica gel, eluting with chloroform/methanol mixtures. The polymer was purified by precipitation from a concentrated chloroform solution into diethyl ether. The white powder was isolated by filtration, and dried under vacuum to yield 11.3 g (75% yield). $^1$H NMR (CDCl$_3$) δ 5.62 (m, 2H), 3.28-3.84 (complex, br m, 228H), 2.54 (br s, 1H), 1.28-2.36 (complex br m, 11H); $^{13}$C NMR (CDCl$_3$) δ 130.2, 129.6, 81.1, 72.7, 71.0, 70.7, 70.4, 67.8, 61.8, 34.2, 33.5, 25.9, 25.8, 22.8; ATR-FTIR 3491, 2882, 1467, 1359, 1341, 1280, 1242, 1100, 1060, 959, 841, 725 cm$^{-1}$; GPC (THF, relative to PEG standards) $M_n$, 2300 Daltons, $M_w$, 2350 Daltons, PDI 1.02.

Example 4

This example describes the preparation of an azidoaryl-substituted cyclooctene by reaction of an acid chloride-substituted phenyl azide with 5-aminocyclooctene. The reactions are illustrated in Scheme 4. 4-Azidobenzoic acid was converted to the corresponding acid chloride (10) with thionyl chloride and triethylamine in dry tetrahydrofuran. An excess of 5-aminocyclooctene was then introduced to the solution of the acid chloride at 0° C. to form the azidoaryl-substituted cyclooctene, 4-azido-N-4-cyclooctene-1-yl-benzamide (9), which was purified by recrystallization from diethyl ether/hexane in 73% yield. The product was characterized by proton and carbon-13 nuclear magnetic resonance spectroscopy ($^1$H and $^{13}$C NMR), as well as Fourier Transform Infrared (FTIR) spectroscopy. Key features in the characterization of 4-azido-N-4-cyclooctene-1-yl-benzamide included the presence of the amide carbonyl in the $^{13}$C NMR spectrum at 165.1 parts per million (ppm), and a characteristic azide signal in the IR spectrum at 2120 reciprocal centimeters (cm$^{-1}$).

A representative synthetic procedure is as follows. 4-Azidobenzoic acid (2.0 grams, 12.2 millimoles) was added to a dry round-bottom flask and diluted with 100 milliliters anhydrous THF under $N_2$. The solution was cooled to 0° C. and thionyl chloride (0.9 milliliters, 12.8 millimoles) was added by syringe over approximately 5 minutes. The reaction mixture was allowed to stir for 1 hour while warming to room temperature. The reaction was again cooled to 0° C. and triethylamine (4.2 milliliters, 24.4 millimoles) was added by syringe. A white precipitate was immediately formed and the mixture was allowed to stir for an additional 15 minutes at 0° C. A solution of 5-aminocyclooctene (1.7 grams, 13.4 millimoles) in 10 milliliters anhydrous THF was then added by syringe and the reaction was warmed to room temperature and stirred for 16 hours. The reaction mixture was filtered over Celite to remove the salt by-products and the solution was concentrated to a light yellow solid. The crude product was dissolved in diethyl ether and washed once with deionized water and once with 1 molar aqueous hydrochloric acid. The organic layer was dried over MgSO$_4$ and concentrated. The resulting solid was purified by recrystallization (diethyl ether/hexane) to afford 2.4 g (73% yield) of product as light yellow crystals. $^1$H NMR (CDCl$_3$) δ 7.74 (d, 2H), 7.02 (d, 2H), 6.23 (br s, 1H), 5.72 (m, 2H), 4.16 (m, 1H), 2.14-2.40 (complex br m, 4H), 1.80-2.01 (complex br m, 2H), 1.50-1.76 (complex br m, 4H); $^{13}$C NMR (CDCl$_3$) δ 165.1, 143.1, 131.5, 130.5, 129.8, 128.7, 128.6, 118.9, 49.9, 35.3, 34.4, 26.0, 25.9, 23.4; ATR-FTIR 3306, 3058, 3023, 2933, 2855, 2410, 1625, 1601, 1571, 1542, 1498, 1337, 1279, 1187, 1149, 1123, 847, 768, 725 cm$^{-1}$.

Scheme 4

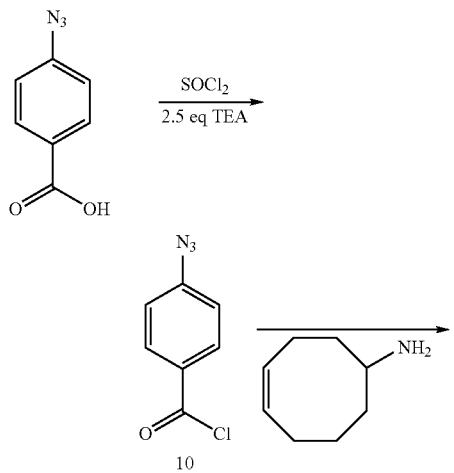

10

-continued

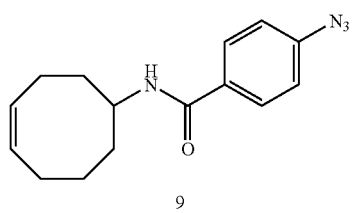

9

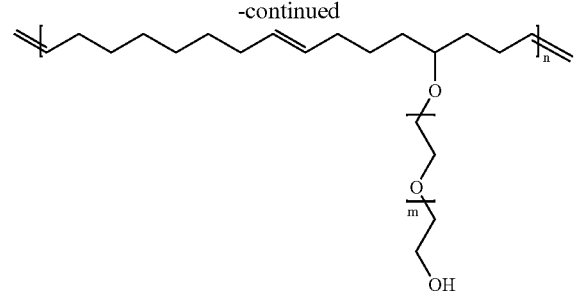

Polymer 6:7:8 ratio

| | |
|---|---|
| 1 | 80:20:0 |
| 2 | 90:10:0 |
| 3 | 92:8:0 |
| 4 | 92:6:2 |
| 5 | 91:8:1 |

Examples 5-9

These examples describe the preparation of poly(cyclooctene-graft-polyethylene glycol) copolymers varying in the chain length and relative concentration of polyethylene glycol grafts. As illustrated in Scheme 5, five graft copolymers were prepared by ring-opening metathesis polymerization (ROMP) of the specified monomers/macromonomers in dichloromethane, using Grubbs' Generation II catalyst (tricyclohexylphosphine[1,3-bis(2,4,6-trimethylphenyl)-4,5-dihydroimidazol-2-ylidene][benzylidine]ruthenium(IV) dichloride; see, M. Scholl, S. Ding, C. W. Lee, R. H. Grubbs, Org. Lett. 1999, volume 1, page 953), with a 250:1 monomer-to-catalyst ratio, and 1-hexene as the chain transfer agent (50:1 molar ratio of monomer-to-chain transfer agent). The polymerization was terminated by addition of ethyl vinyl ether, and the polymer was isolated as a powder following precipitation into cold hexane. Gel permeation chromatography (GPC), using linear polystyrene standards and tetrahydrofuran as eluent, was used to estimate the molecular weights and polydispersities of the graft copolymers, as presented in Table 1 (which follows the description of Examples 11-15). As expected for polymers prepared by ROMP with this catalyst, the polydispersity of these samples was estimated by GPC to be about 2. Importantly, the copolymers obtained by this process, as characterized by NMR spectroscopy, show a ratio of comonomer incorporation into the graft copolymer in accord with the comonomer feed ratio employed.

Scheme 5

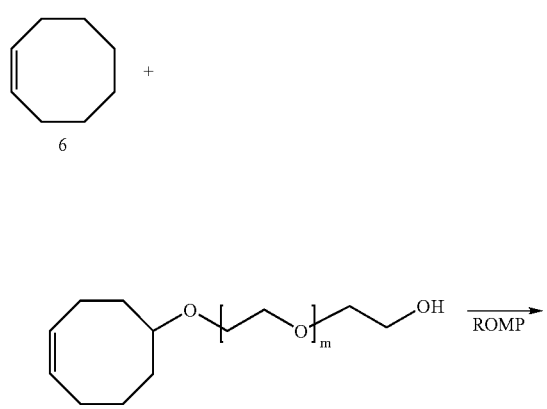

7: m ~ 24
8: m ~ 49

Example 10

This example describes the preparation of a ROMP copolymer of cyclooctene, PEGylated cyclooctene, and azidoaryl-substituted cyclooctene. 4-Azido-N-4-cycloocten-1-yl-benzamide, prepared as described in Example 4, was integrated into poly(cyclooctene-graft-PEG) copolymers by the ROMP copolymerization shown in Scheme 6 to give the desired graft copolymer, using Grubbs' Generation III catalyst (3-bromopyridine substituted ruthenium benzylidene, (IMesH$_2$)(Cl$_2$)(C$_5$H$_5$N)$_2$Ru=CHPh; see, J. A. Love, J. P. Morgan, T. M. Trnka, R. H. Grubbs, Angew. Chem. Int. Ed. 2002, volume 41, pages 4035-4037). For the membranes prepared as described below, the graft copolymer was prepared from 20 mole percent azidoaryl-substituted cyclooctene, 60 mole percent cyclooctene, and 20 mole percent PEGylated cyclooctene 11 with PEG molecular weight of about 4400 grams per mole (about 100 ethylene oxide repeat units). The composition of this amphiphilic graft copolymer proved convenient for coating poly(vinylidene fluoride) ultrafiltration (PVDF-UF) membranes, as this copolymer is soluble in ethanol, a suitable solvent for solution-based coating of PVDF-UF membranes (and other commercial membranes), and also provided sufficient phenyl azide functionality for effective crosslinking of the coating. Typical preparations of the graft copolymer gave materials that by gel permeation chromatography (GPC) in tetrahydrofuran appeared as a single Gaussian peak, having number-average molecular weights of about 35,000 g/mol, and polydispersity index (PDI) values of about 1.7. $^1$H NMR spectroscopy performed on deuterated chloroform (CDCl$_3$) solutions of the graft copolymer showed backbone olefin resonances at about 5.4 ppm, in the typical region for poly(cyclooctene)-based polymers, and no evidence of residual cyclooctene monomers in the characteristic region of about 5.7 ppm. Aromatic resonances of the phenyl azide group were observed at 7.04 and 8.00 ppm, and integrated against protons of the polymer backbone protons to confirm the expected mole percent incorporation. FTIR spectroscopy on the graft copolymer showed a diagnostic azide stretch at about 2100 cm$^{-1}$. This synthetic strategy connects the reactive azide functionality to the polymer backbone through an amide bond which, like the ether connectivity of the PEG chains, is stable hydrolytically and thus well-suited for aqueous-based membrane applications. We also prepared several combinations of polymers of type 12, by fixing the PEGylated cyclooctene at 20 mole percent, and varying the azidoaryl cyclooctene from 5-15 mole percent, and cyclooctene from 65-75 mole percent.

However, these graft copolymer exhibited reduced solubility in ethanol. Although these graft copolymers were more soluble in chloroform and toluene, these solvents are less suitable for coating on some underlying membrane supports. Thus, the composite membrane experiments described herein were performed with polymer 12 having 60 mole percent cyclooctene, 20 mole percent PEGylated cyclooctene (PEG graft molecular weight about 4400), and 20 mole percent azidoaryl-substituted cyclooctene.

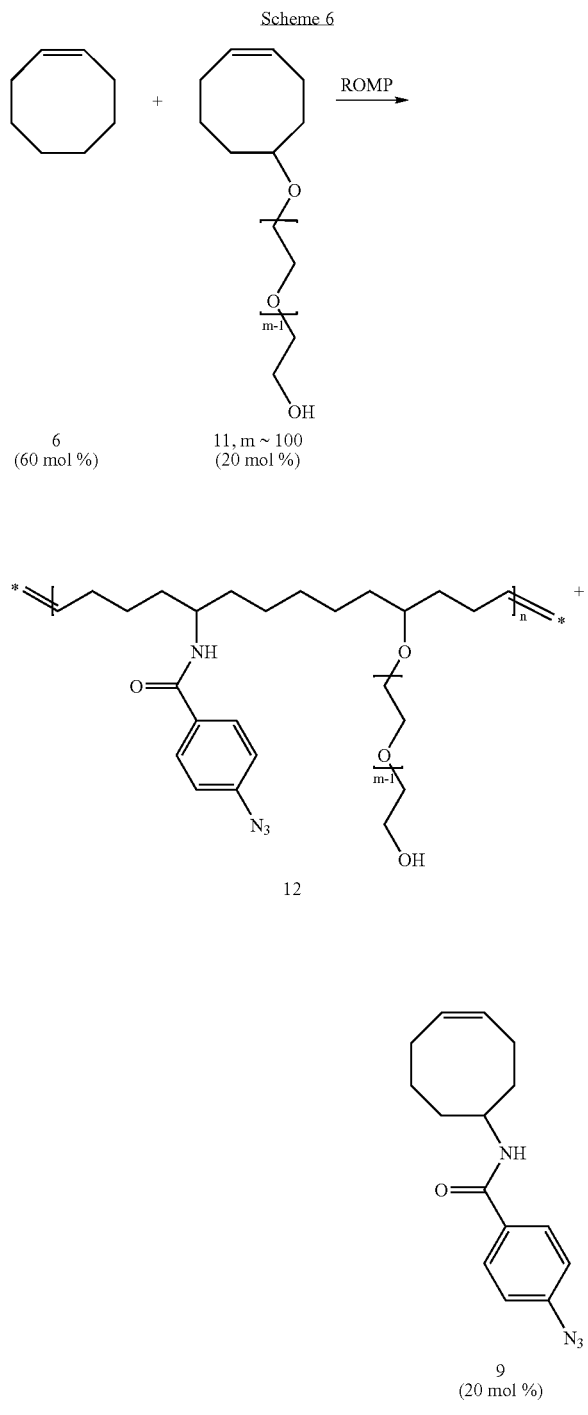

Examples 11-15

Before applying polyolefin-graft-PEG copolymers as coatings to PVDF-UF membranes, dense films of the copolymers were prepared and characterized in terms of pure water uptake and pure water flux under dead-end flow conditions. Such characterization is important for determining coating compositions that possess sufficient hydrophilicity for water purification applications. Dense film membranes of polyolefin-graft-PEG copolymers 1-5 were prepared by casting films from 20 weight percent toluene solutions of the copolymers onto glass plates, then drawing the films to the desired thicknesses using a Gardco film applicator. Residual solvent was removed from the films by allowing them stand at room temperature, then exposing them to vacuum (about 13 Pascals (100 millitorr) absolute pressure) at room temperature. For the preparation of crosslinked polymer films, ring-opening cross-metathesis was employed. See K. Breitenkamp, J. Simeone, E. Jin, T. Emrick, *Macromolecules* 2002, volume 35, page 9249. In this method, a toluene solution was prepared containing about 20 weight percent of the graft copolymer, and about 7 weight percent of a bis-cyclooctene PEG (see K. Breitenkamp, T. Emrick, *J. Am. Chem. Soc.* 2003, volume 125, page 12070), to which was added a toluene solution of Grubbs' Generation II catalyst (about 3 milligrams) under constant agitation. As crosslinking occurs quickly using this method, the mixture was cast immediately on a glass slide to give the desired membrane as a crosslinked dense film of thickness about 50 micrometers. This crosslinking imparted the dense films with far more robust properties than seen when attempting to prepare films without crosslinking. Moreover, degree of crosslinking provides a means by which water uptake can be controlled.

As shown in Table 1, poly(cyclooctene-graft-PEG) membranes could be prepared with variable hydrophilicity, as indicated by the water uptake values. In copolymers containing lower PEG-grafting density (that is, from 1-8 mole percent PEG 1,100 g/mol and/or PEG 2,200 g/mol), water uptake values in the 40-70% range were observed. Steady state water uptake values were obtained by dividing the difference in weight of the wet (soaked in water) and dry membranes by that of the dry membrane. These cross-linked membranes exhibited, qualitatively, appreciable mechanical properties, such that they could be removed from the glass plate onto which they were cast, and handled without tearing. Poly(cyclooctene)-graft-PEG copolymer membranes with higher PEG densities, for example 20 mole percent of PEG 1,100 g/mol, possessed very high water uptake values (200% or more). However, copolymer films with such high PEG content were not mechanically robust, and thus required crosslinking and/or an underlying substrate for effective application to water purification membranes. Increasing PEG density in the poly(cyclooctene-graft-PEG) copolymer dense films was associated with enhanced pure water flux, using an Amicon stirred cell in a dead-end flow setup. As provided in Table 1, the pure water permeance is directly related to percent water sorption. For polymers 4 and 5, having similar weight percent PEG, the films obtained were seen to have appreciable differences in water sorption and flux values. This may, however, not be an intrinsic property of the polymer composition, but rather due to variation in crosslinking efficiency from sample-to-sample. Nonetheless, it does appear that the integration of PEG 2,200 g/mol into the copolymer structures has a positive effect on both water sorption and flux.

TABLE 1

Characterization of polyolefin-graft-PEG copolymers with different mole percentages of monomers 6-8 (where 6 = cyclooctene, 7 = PEG-1100 cyclooctene macromonomer, and 8 = PEG-2200 cyclooctene macromonomer). Polymer solution was added with about 7 weight percent of a bis-cyclooctene PEG. The membrane thickness was about 50 micrometers.

| Polymer[a] | Molar ratio 6:7:8 | PEG weight percent | $M_n$ (GPC[b]) | PDI ($M_w/M_n$) | Water uptake (wt %) |
|---|---|---|---|---|---|
| 1 | 80:20:0 | 73 | 42,800 | 1.9 | 220-240 |
| 2 | 90:10:0 | 55 | 34,400 | 2.0 | 60-70 |
| 3 | 92:8:0 | 49 | 15,800 | 1.6 | 50-60 |
| 4 | 92:6:2 | 53 | 22,700 | 1.8 | 45-50 |
| 5 | 91:8:1 | 54 | 27,800 | 2.1 | 40-45 |

[a][M] = 2.0 mol/L, [M]/[Cat] = 500, [M]/[1-Hexene] = 100, 40° C. in $CH_2Cl_2$.
[b]GPC in $CHCl_3$ versus polystyrene standards.

Examples 16-20

These examples illustrate the effect of crosslinker concentration on both water flux and sorption values. Membranes prepared from polymer 5 in the absence of crosslinking exhibit high water sorption and flux values. As seen in Table 2, water sorption and flux drops to about 50% of the initial value with about 2 weight percent crosslinker. This control over sorption and flux continues to about 7 weight percent crosslinker, at which point a lower limit of water flux and sorption appears at about one-third the initial level. Additional experiments with these dense films were conducted to analyze the effect of crosslinker weight percent on water flux values obtained at various feed pressures in a dead-end flow setup. This is seen in FIG. 1. From the dense membrane without any crosslinker, a measurable permeate was collected at a feed pressure of only 10 pounds per square inch (69 kilopascals). The effect of percent crosslinker used on the feed pressure needed to obtain constant water flux shows that an appreciable level of control over flux can be obtained in these films, and that even upon crosslinking, sufficient water flux is observed such that application of these materials as coatings on commercial membranes is feasible.

TABLE 2

Effect of bis-cyclooctene PEG crosslinker concentration on percent water sorption and water permeance through the membranes prepared from polymer 5. The membrane thickness was about 50 micrometers. Water flux experiments were carried out with an Amicon stirred cell under dead-end flow.

| Crosslinker (wt %) | Water sorption (wt %) | Average water permeance (LMH/atm) |
|---|---|---|
| 0 | 108 | 11.0 |
| 2 | 65 | 6.2 |
| 5 | 50 | 3.7 |
| 7 | 42 | 3.0 |
| 12 | 40 | 2.8 |

Examples 21-24

Figure 2:
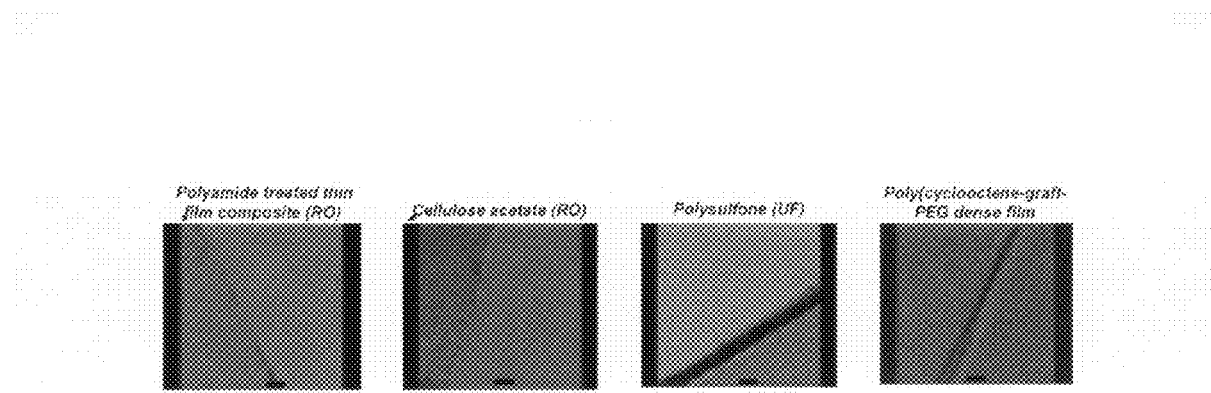
FIG. 2 shows fluorescence confocal microscopy images of protein adsorption (fluorescein-BSA in aqueous buffer solution at pH 7.4) on a dense film of polyolefin-graft-PEG (far right), and on commercial samples of treated polyamide (far left), cellulose acetate (second from left), and polysulfone (third from left); the green color arises from the fluorescence of the dye-labeled protein; the polyolefin-graft-PEG copolymer exhibits very little fouling relative to the commercial membranes; the black bar in each image is 50 micrometers.

These examples describe evaluation of various films for adsorption of bovine serum albumin. Poly(cyclooctene)-graft-PEG copolymer films, when tested against bovine serum albumin (BSA) solutions in the Bradford titration method (see, M. M. Bradford, *Analy. Biochem.* 1976, volume 72, page 248), showed very low levels of protein adsorption (about 1 microgram per square-centimeter). In fact, the appreciable anti-fouling properties of these graft copolymer films made protein adsorption difficult to quantify by this method. This contrasts with the situation for many commercial membranes, such as polysulfone and polyamide membranes, in which protein adsorption is appreciable and readily quantified (typical reported values range between 10 and 50 micrograms per square-centimeter). Fluorescence confocal laser scanning microscopy provides an alternative visual method to evaluate fouling on both commercial and novel synthetic membranes. See M. Ferrando, A. Rozek, M. Zator, F. Lopez, C. J. Guell, *J. Membr. Sci.* 2005, volume 250, page 283. FIG. 2 shows fluorescence confocal microscope images of several membranes following exposure to aqueous solutions of fluorescent BSA. These membranes were cut as about 2 centimeter square sections from polyamide reverse osmosis (RO) thin film composite membranes, cellulose acetate asymmetric RO membranes, polysulfone UF membranes, and polyolefin-graft-PEG dense films. The membranes were immersed in a phosphate buffered saline (PBS, pH 7.4) solution of fluorescein-conjugated BSA (0.02 milligrams/milliliter) for 24 hours, followed by rinsing with PBS. As shown in FIG. 2, confocal fluorescence images of these membranes (excitation at 488 nanometers) reveal striking and obvious visual differences in protein adsorption on the commercial membranes relative to the PEGylated graft copolymer film. The polyolefin-graft-PEG membrane sample used these experiments contained 54 weight percent PEG (polymer 5), a modest level of PEGylation, yet clearly sufficient for resisting fouling. These results show that the PEGylated graft copolymers are well suited to prevent protein fouling.

Example 25

This example describes the coating of a poly(cyclooctene-graft-PEG) copolymer layer on a PVDF-UF membrane and subsequent crosslinking of the copolymer layer. In initial studies, composite membranes were prepared by coating PVDF-UF membranes with poly(cyclooctene-graft-PEG) copolymers, followed by placement of the composite membranes in a cross-flow unit at 150 pounds per square inch (1034 kilopascals). However, in the early stages of cross-flow experiments, delamination of the graft copolymer coating from the membrane support was observed. While not wishing to be bound by any particular theory, the inventors speculate that the substantial hydrophilicity of the coating leads to its swelling, and overcomes its adhesion to the underlying PVDF support. Moreover, the present inventors found that crosslinking strategies using the bis-cyclooctene crosslinkers (as described, for example, in U.S. Patent Application Publication No. US 2005/0096454 A1 of Emrick et al.) were not easily applied to cases involving underlying support membranes, due to the formation of bubbles that led to defects within the coating. Thus, a different method was sought to generate the desired composite membranes, in which the coating and crosslinking steps were conducted separately, by incorporating UV-reactive azidoaryl groups into the copolymer structure. For this, graft copolymers containing azidoaryl pendant groups were used.

The PVDF-UF membranes used in this study were purchased from Sterlitech, Inc. The scanning electron micrograph (SEM) images of the top surface of these membranes shown in FIG. 3 reveal sub-micron pores on the top surface of the membrane. For the coating procedure, an ethanol solution of graft copolymer 12 (about 50 milligrams/milliliter, $M_n$ ~35,000 g/mole, PDI 1.7) was applied by spin coating onto the PVDF membrane to give a sub-micron graft copolymer coating. The coated membrane was then placed in an ultraviolet (UV) light source box (UVP, Inc.) and irradiated at ~302 nanometers for 6 minutes. This irradiation step is believed to convert the phenyl azide (Ph-N$_3$) groups into phenyl nitrenes (Ph-N:) by loss of nitrogen gas. The nitrenes generated in this process are highly reactive (see, for example, D. S. Breslow, In *Azides and Nitrenes—Reactivity and Utility*; E. V. S. Scriven, Ed. Academic Press: Orlando, Fla., 1984; pp 491-517; J. Brunner, *Annu. Rev. Biochem.* 1993, volume 62, page 483), and can insert into olefins in the polymer backbone to give aziridines, as well as C—H bonds in the polymer backbone and grafts, and possibly in the underlying PVDF-UF support, to give amines. This UV-induced crosslinking proved successful for stabilizing the graft copolymer coating on the PVDF-UF membrane surface, and it eliminated problems associated with rapid delamination of the coating during cross-flow. Attenuated total reflectance Fourier transform infrared spectroscopy (ATR-FTIR) performed on the composite membrane following irradiation was used to confirm the complete disappearance of diagnostic azide stretch at about 2100 cm$^{-1}$ in the graft copolymer structure.

Examples 26-32

Figure 4:
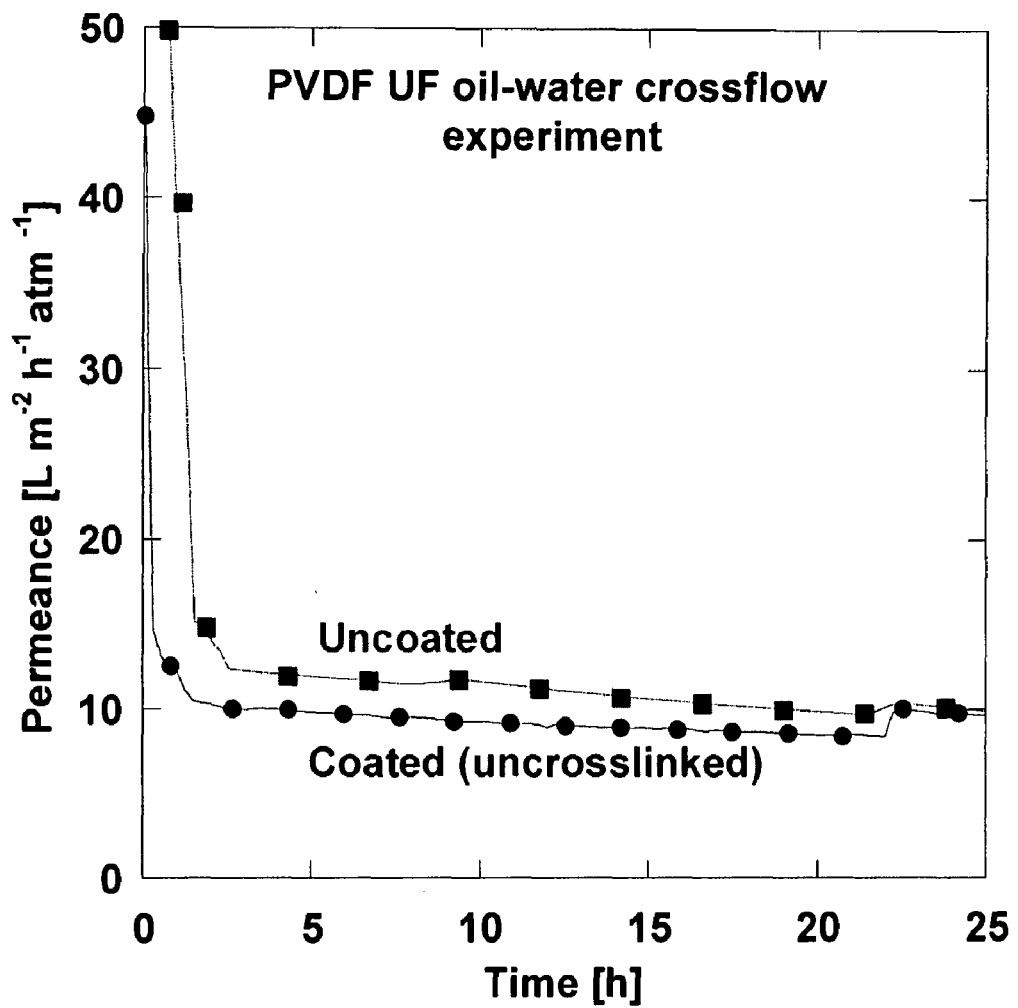
FIG. 4 shows cross-flow experimental results with an uncoated PVDF-UF membrane (squares) and an uncrosslinked graft copolymer 5 coated membrane (circles).
Figure 5:
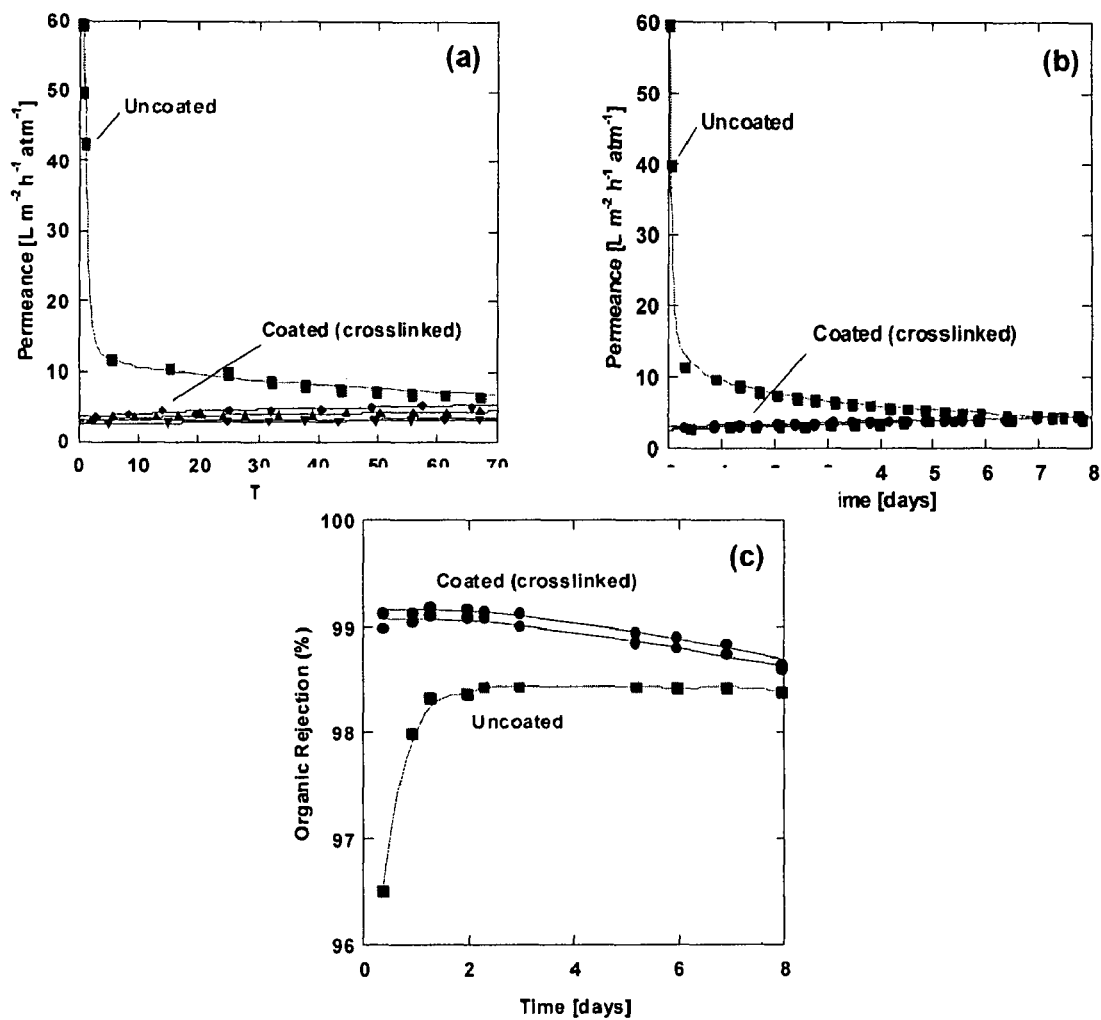
FIG. 5 shows cross-flow experimental results with an uncoated PVDF-UF membrane and a crosslinked graft copolymer coated membrane: a) flux values obtained using membranes coated with a crosslinked coating of graft copolymer 12; b) continuation of cross-flow experiment to eight days; c) oil rejection values; in each plot, data for the uncoated membrane are shown as squares, and data for the coated membrane are shown as circles.
Figure 6:
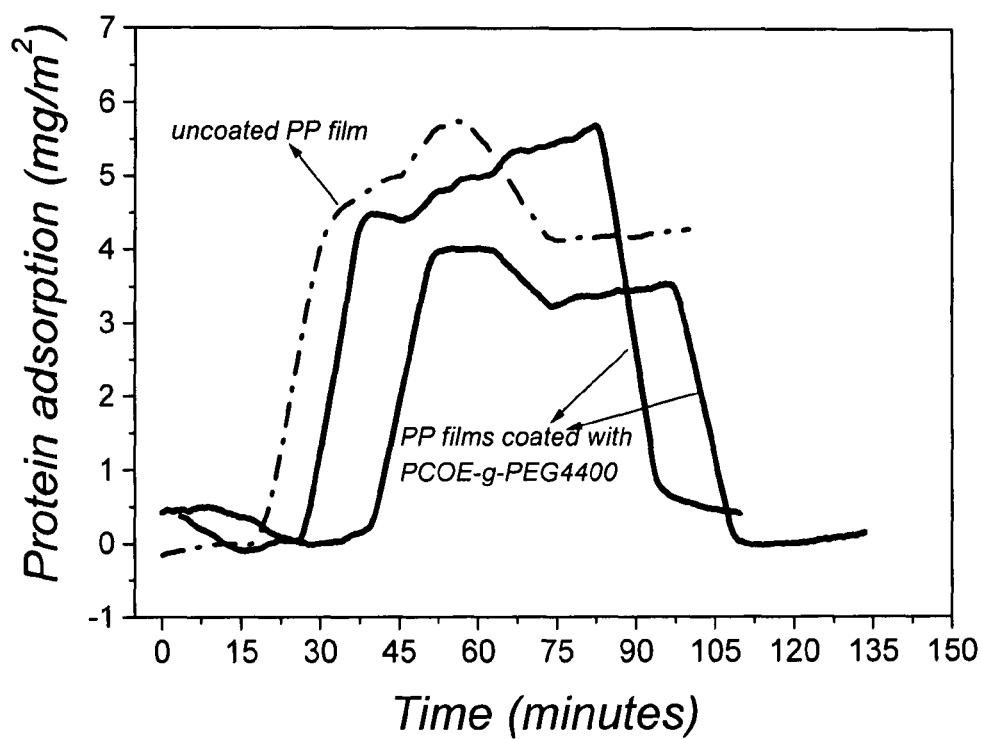
FIG. 6 shows protein absorption on uncoated (dot-dash line) and copolymer-coated (solid lines; the film with the higher protein absorption before washing was exposed to a more concentrated protein solution (ca. 200 ppm) than the film with the lower protein absorption before washing (ca. 150 ppm)) polypropylene films exposed to fluorescein-labeled fibrinogen in buffer solution; protein concentrations were determined using total internal reflection fluorescence methods; exposure to protein solution begins at about 25-35 minutes and ends at about 90-100 minutes, and it is preceded and followed by exposure to protein-free buffer solution; in the case of copolymer-coated polypropylene films, protein is easily removed as noted by the drop in protein adsorption to near zero after about 105 minutes; for the uncoated polypropylene film, the protein is irreversibly adsorbed.

These examples describe cross-flow experiments on graft copolymer-coated PVDF-UF composite membranes. Cross-flow experiments on both uncoated and graft copolymer-coated PVDF-UF membranes were conducted at a feed pressure of 150 pounds per square inch (1034 kilopascals), and a cross-flow velocity of 0.5 gallons per minute (GPM; 1.89 liters per minute). The feed solution consisted of a 1500 ppm oil-in-water emulsion (9:1 ratio of soybean oil:DC 193 surfactant obtained from The Dow Chemical Company), prepared by mixing the oil, water, and surfactant in a blender at 3000 rotations per minute for about 3 minutes to give a homogeneous emulsion. Periodic evaluation of the oil concentration was carried out using a total organic compounds (TOC) analyzer (Shimadzu TOC-5050A). It was immediately seen that the delamination problem observed for graft copolymers 1-5 during the cross-flow operation was not seen in the irradiated composite membranes prepared from azidoaryl-functionalized graft copolymer 12, despite the very high (>80 wt %) weight percent of PEG in the polymer coating. Control experiments confirmed the importance of the azide groups. For example, a PVDF-UF membrane was coated with a graft copolymer containing an 80:20 molar ratio of cyclooctene and PEG-4400 cyclooctene macromonomer 11, followed by an irradiation step identical to that used for the azide-containing coating. Cross-flow experiments with oil-water emulsion feed solutions carried out with these uncrosslinked copolymer coatings led to rapid membrane fouling, and thus minimal positive influence of the coating. This is shown in FIG. 4, in which the uncoated and coated PVDF supports follow the same trend—decreasing flux as a function of time, due to membrane fouling. Water contact angle measurements taken on the membrane surface after cross-flow (about 60 to 65°) were quite close to those of the uncoated membrane (about 64 to 67°), confirming the loss of graft copolymer from the surface, and much higher than membranes with stable crosslinked graft copolymer coatings (FIG. 5). Thus, subsequent experiments exclusively used the azidoaryl-functionalized amphiphilic graft polymer.

Cross-flow experiments were then performed to compare the uncoated PVDF-UF membranes to those coated with a crosslinked film of graft copolymer 12, again using oil-in-water emulsions at 150 pounds per square inch (1034 kilopascals) feed pressure and 0.5 GPM cross-flow velocity. The ability of the graft copolymer coated membranes to resist fouling relative to the uncoated PVDF-UF membranes is seen in FIG. 5. In FIG. 5a, four different graft copolymer coated membranes are represented by the four dashed lines, in which each coating is of slightly different thickness. The performance of these coated membranes is compared to an uncoated PVDF-UF membrane over a period of three days. While the composite membranes exhibit an expected drop in initial flux as a consequence of the coating, all of the coated membranes maintain a relatively stable flux from about two hours through the end of the plotted timeframe. On the other hand, the uncoated PVDF membrane shows a considerable decline in flux during the same period, from about 14 LMH/atm to about 6-7 LMH/atm. When this coated versus uncoated competitive membrane experiments are extended to longer time periods, as shown in FIG. 5b, a cross-over is seen, such that water flux through the coated membrane equals and then exceeds that of the uncoated membrane. Ultimately, the uncoated membrane is expected to approach zero flux at some time period, due to complete fouling. This result carries considerable significance given the long usage lifetime desired for membranes of this type, and the stability against oil droplet fouling provided by the graft copolymer coating. Interestingly, in some cases the observed flux of the graft copolymer coated membrane increases slightly over the measured period. This may be due to some loss of the graft copolymer in areas of the membrane where crosslinking was inefficient, either on the membrane surface, or perhaps more likely in areas where the polymer had penetrated the membrane pores. No matter the cause of this increased flux, it is not seen to lead to rapid fouling. Finally, as shown in FIG. 5c, the graft copolymer coating was seen to improve the rejection of oil droplets, as determined by analysis of the permeate. The uncoated PVDF-UF membranes provide increasing oil droplet rejection as a consequence of fouling, while the graft copolymer coated membranes maintained 99-98.5% rejection during the course of the experiment.

Figure 3:
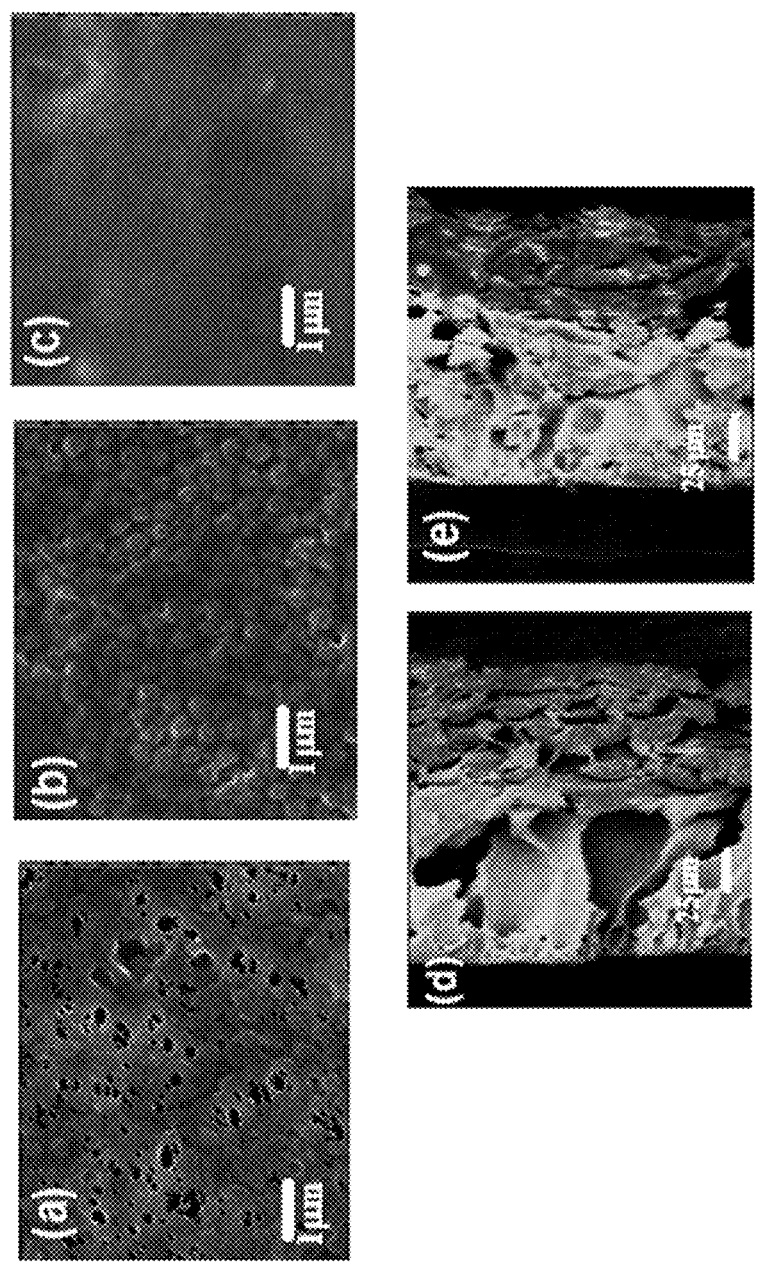
FIG. 3 shows scanning electron microscopy (SEM) images of poly(vinylidene fluoride) ultrafiltration membranes (PVDF-UF membranes): (a) Top view before coating; (b) top view after coating with graft copolymer 12 and UV-irradiation; (c) top view after cross-flow experiments; (d) cross-section before coating with 12; (e) cross-section after coating with 12.

FIG. 3 shows SEM images of the top surface (FIG. 3a) of the commercial and coated (FIG. 3b) PVDF-UF membranes used in this study. SEM shows convincingly that the graft copolymer coating completely covers the membrane pore structure. Cross-sectional SEM images of the coated membrane confirm that pore penetration of the graft copolymer into the membrane does occur (FIGS. 3d and 3e). While the presence of the graft copolymer on the membrane surface, and in the inner-pore structure, is expected to lower the initial flux of the membranes, the substantial hydrophilicity of the graft copolymer used in the coating process leads to only a moderate initial flux decline that can eventually be overcome by the reduction in fouling over time relative to the uncoated membranes. Importantly, the graft copolymer coating remains intact on the support throughout the cross-flow experiments. This is confirmed in the SEM image of FIG. 3c, taken on the composite membrane following removal from the cross-flow unit. In addition, it seems that a smoother membrane surface in the coated composite is present following cross-flow experiments. This may be associated with some loss of graft copolymer coating during the cross-flow operation, but is more likely a result of reorganization of the graft polymer during and after the cross-flow experiment. Nevertheless, after the cross-flow operation, the water contact angle of the coated composite membrane (44-46°) remains identical to that before the cross-flow, and is considerably lower than that of the uncoated membrane (64-67°).

Examples 33-36

These examples illustrate the ability of the present copolymers to function as anti-fouling coatings for solid surfaces. Specifically, anti-fouling activity on polypropylene and alkane-functionalized glass is demonstrated.

Enhanced protein fouling resistance was observed in polypropylene and modified glass slides coated with UV-cross-linked azidoaryl-substituted, PEG-functionalized polycyclooctene (PCOE), relative to the unmodified substrates. For example, a 200 ppm fluorescein-labeled fibrinogen solution in 10 mM phosphate buffer at pH 7.0 was passed under gentle shear flow (to avoid protein denaturation) onto a polypropylene film. The film was equilibrated/flushed with only buffer solution for 30-45 minutes before and after exposure to protein solution. The post-protein exposure flushing step removes excess or weakly attached protein from the surface of the film. The protein concentration was measured by a pre-calibrated Total Internal Reflection Fluorescence (TIRF) method. The TIRF measurement indicated the presence of about 5 mg/m$^2$ fibrinogen on an uncoated polypropylene surface, while the coated polypropylene surface showed negligible protein content.

Similar experiments were conducted with an alkane modified glass, which was prepared as follows. Clean glass slides were treated with Piranha solution (70 volume percent sulfuric acid, 30 volume percent hydrogen peroxide), then immersed for about 30 minutes in 2 weight percent hexadecyltrichlorosilane dissolved in toluene. After repeated washing with toluene, the glass slides were kept in oven at 100° C. for 5 minutes. The alkane-modified glass was used as a model hydrophobic substrate. Without a coating of graft copolymer, about 13 mg/m$^2$ fibrinogen adsorbed to the alkane-modified glass. However, the graft copolymer coated glass slides showed only about 0.3 mg/m$^2$ fibrinogen adsorption.

These experiments demonstrate quantitatively the anti-fouling properties of the PEGylated coating and are in accord with the qualitative observations made on coated PVDF-UF membranes by fluorescence confocal microscopy. Moreover, these experiments confirm that the oil-droplet fouling prevented in the PVDF-UF case extends to the prevention of protein fouling.

Examples 37 and 38

These experiments demonstrate the anti-fouling activity of the present copolymer when coating on microfiltration membranes.

Figure 7:
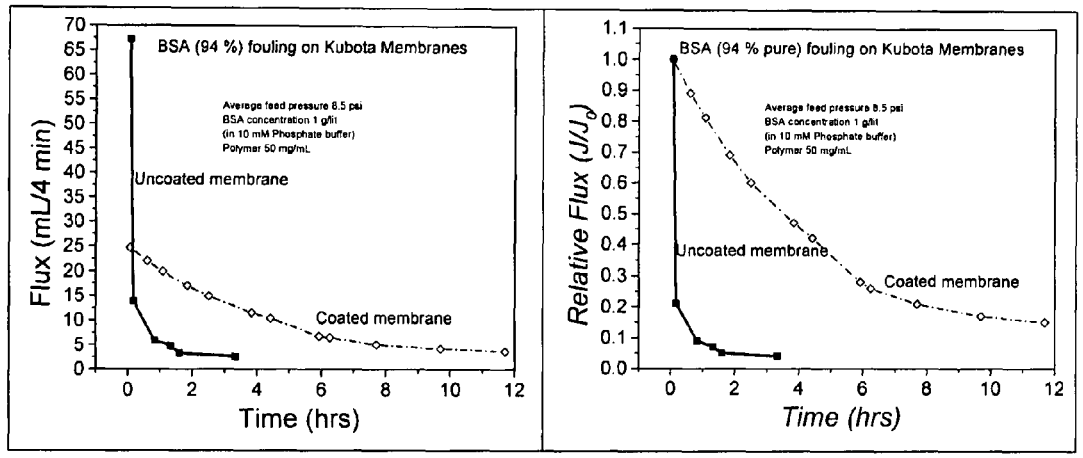
FIGS. 7 and 8 show protein fouling of microfiltration membranes using protein solution feed pressures of 8 and 11 pounds per square inch, respectively; for each of FIGS. 7 and 8, the left plot shows the absolute fluxes for uncoated (solid line) and coated (dot-dash line) microfiltration membranes, and the right plot shows the relative fluxes (normalized to initial flux) for uncoated (solid line) and coated (dot-dash line) microfiltration membranes.
Figure 8:
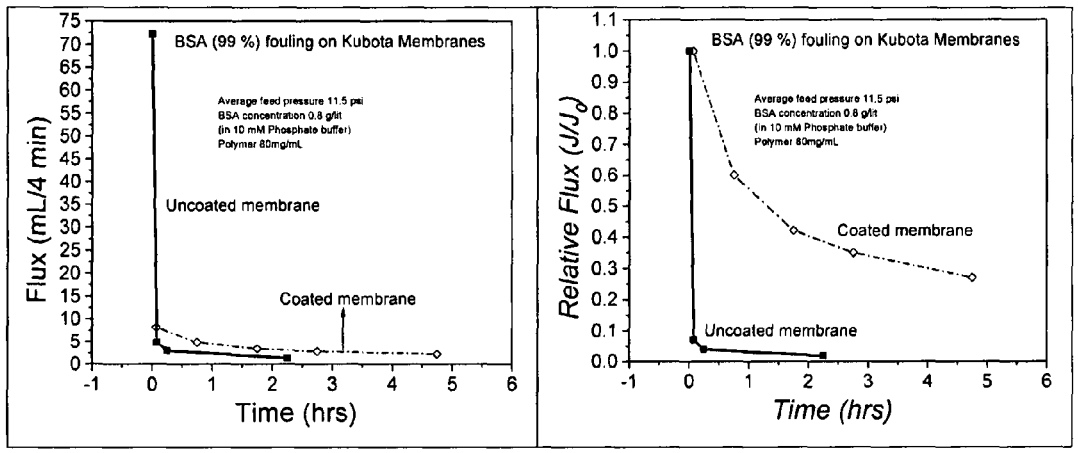

The protein fouling experiments described in Examples 33-36 were extended to Microfiltration (MF) membranes supplied by Kubota, Inc. In general, MF membranes possess a larger average pore size relative to UF membranes. For the current study, we used coated and uncoated Kubota MF membranes (nominal pore size about 0.4 microns) in protein fouling experiments using bovine serum albumin (BSA). The protein feed solution was prepared by dissolving about 1 gram of BSA in 1 Liter of 10 mM phosphate buffer solution maintained at pH 7. Protein fouling experiments were carried-out with a dead-end set-up using an Amican test cell. An ethanol solution of azidoaryl-functionalized PCOE-g-PEG4400 (~50-100 mg/mL) was drop cast onto the Kubota membrane. The drop-casting method was employed to ensure a homogeneous coating coverage on the membrane surface. As in the other cases, the coatings were fixed by UV cross-linking. FIGS. 7 and 8 represent BSA fouling experiments performed at 8 and 11 pounds per square inch (psi) feed pressures, respectively. The solid lines correspond to uncoated Kubota membranes, and the dotted lines to the coated membranes. For the uncoated Kubota membranes, a flux reduction of over 80% was observed in first 5-10 minutes of operation. In the same time period, only a 10-15% flux reduction was observed with the coated composite membranes. Similarly, with the uncoated membrane, complete fouling and flux loss is seen after about 2 hours of operation. In contrast, after 2 hours of operation, the coated membrane retained about 50% of initial flux. The relative flux decrease shown in the right plots of FIGS. 7 and 8 was calculated by dividing the protein solution flux measured at various times (J) with that of pure buffer flux ($J_0$). Note that at both operating pressures and compared to the uncoated membrane, the coated membrane has a lower initial flux but a higher flux after a few minutes of operation.

Examples 39-42

These examples demonstrate the anti-fouling activity of copolymer-coated poly(vinylidene fluoride) and polysulfones ultrafiltration membranes in the presence of an oil-water emulsion feed solution.

Figure 9:
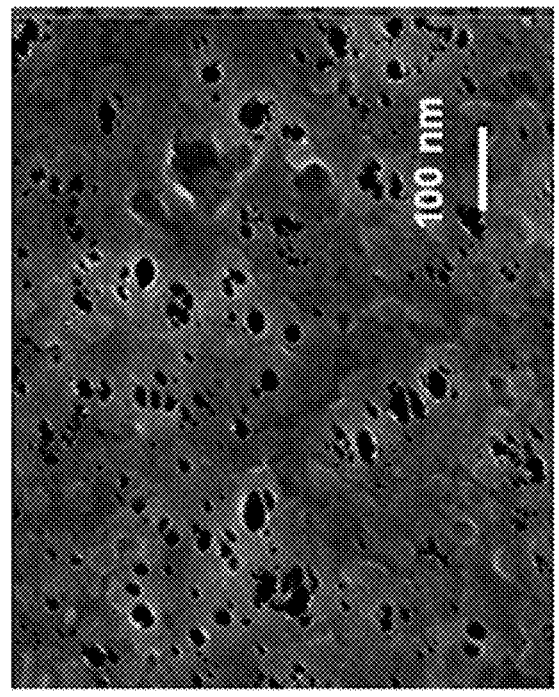
FIG. 9 shows SEM images of the top surfaces of (uncoated) PVDF-UF membranes obtained from (a) Millipore and (b) Sterlitech.
Figure 9:
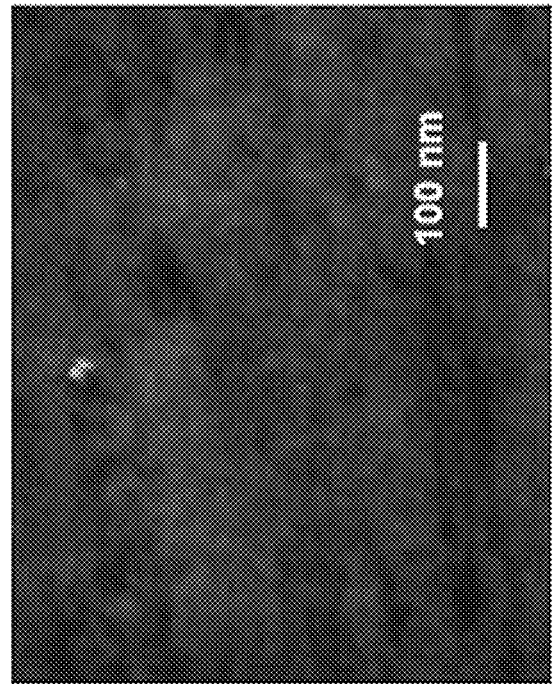
Figure 10:
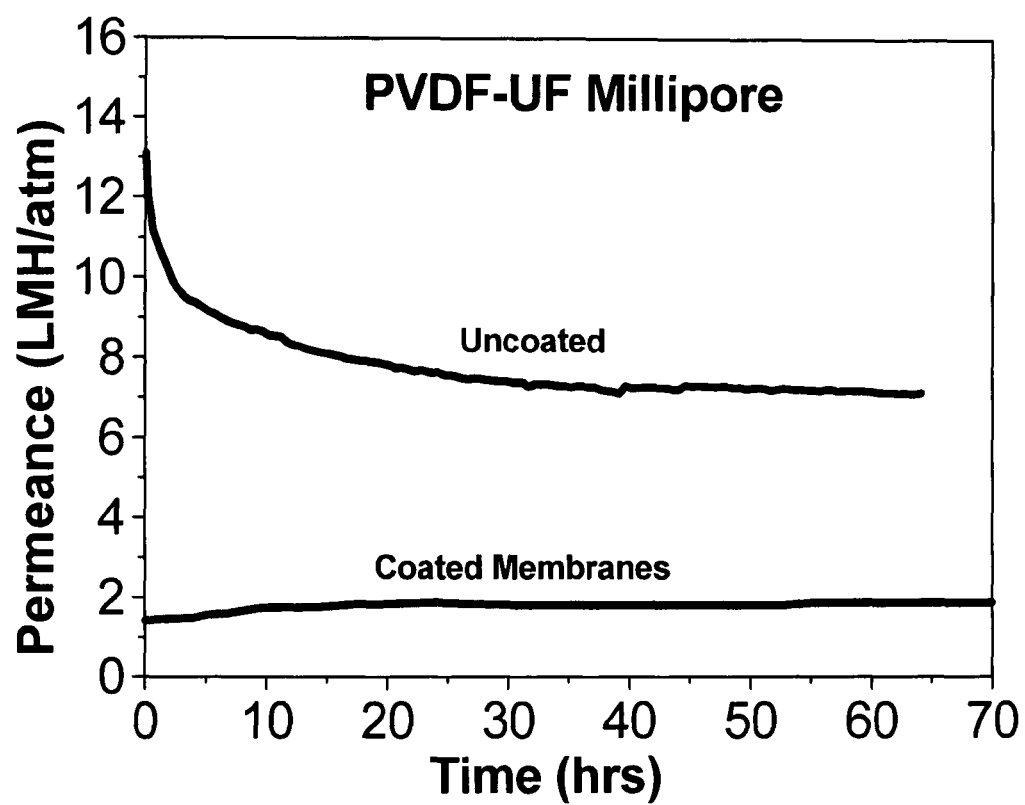
FIG. 10 shows cross-flow experiments for uncoated and coated PVDF-UF membranes in the presence of an oil-in-water emulsion feed solution.

Asymmetric poly(vinylidene fluoride) ultrafiltration membranes (PVDF-UF membranes) without and with a copolymer coating were tested for antifouling activity in the presence of an oil-water solution. The PVDF-UF membranes were obtained from Millipore, Inc. and Sterlitech. Coating and cross-flow experiments were also done with asymmetric PVDF-UF membranes obtained from Millipore Corporation. FIG. 9 shows SEM images of the top surfaces of PVDF-UF membranes obtained from Millipore and Sterlitech. The SEM characterization shows that the Millipore membranes possess a relatively smooth, non-porous surface. A 5 weight percent solution of azidoaryl-functionalized PEGylated polyolefin was spin-coated on the top surface of the Millipore PVDF-UF membrane and UV-irradiated to cross-link the coating. Cross-flow experiments were conducted for about 70 hours with the oil-water emulsion feed solution described above for Examples 26-32 on both coated and uncoated membranes. Results are shown in FIG. 10. During the first 15 minutes of operation, the flux of uncoated membrane decreased from an initial value of about 14 LMH/atm to about 10 LMH/atm, and at longer times a gradual reduction was observed due to fouling. The flux value measured after 60 hours of operation was about 8 LMH/atm. However, no such flux reduction was observed with the coated PVDF-UF membrane. The membrane retained its original flux value of ~2 LMH/atm during the entire 70 hour operation period.

Figure 11:
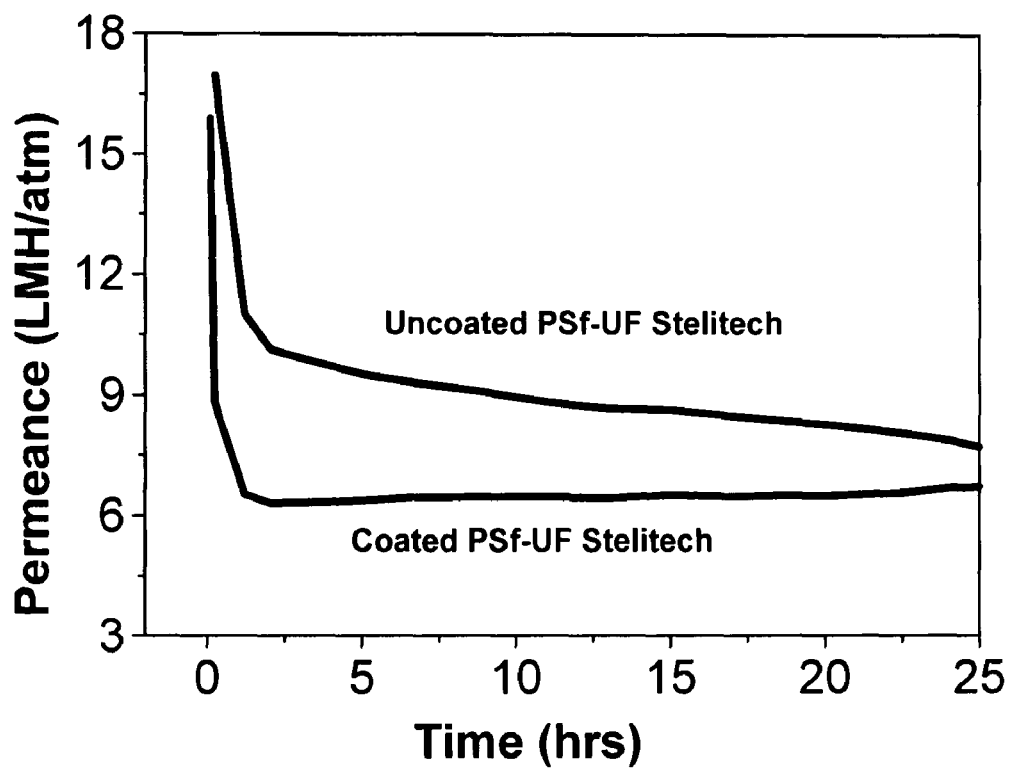
FIG. 11 shows cross-flow experiments for uncoated and coated polysulfone ultrafiltration (PSf-UF) membranes in the presence of an oil-in-water emulsion feed solution.

Similar results were also obtained with another type of UF membrane made from polysulfone (PSf-UF) and manufactured by Sterlitech (FIG. 11). After an initial drop in flux, the coated membrane's flux remains essentially constant at about 6 LMH/atm for the duration of the 24 hour experiment. The present inventors speculate that the initial drop in flux can be attributed to defects in the coating layer, thereby allowing areas of the underlying porous support to come into direct contact with the oil-water feed, which led to a quick drop in flux. However, once the defects have been fouled, nearly all water transport occurs through the coated part of the membrane, and, therefore, no further fouling is seen. Also as shown in FIG. 11, the uncoated PSf-UF membrane exhibited a steady decrease in flux during the entire period of operation.

In summary, a poly(cyclooctene-graft-PEG) copolymer has been synthesized and applied as an anti-fouling coating for water purification membranes. Problems associated with delamination of the graft copolymer from the underlying membrane were overcome using azidoaryl-functionalized polymers for UV-irradiation and crosslinking on a membrane support. Cross-flow experiments conducted with oil-in-water emulsions and protein solutions confirmed that the graft copolymer coating prevents fouling and leads to the eventual increased flux compared to the uncoated commercial membranes. The graft copolymer can also be used as an antifouling coating on solid (non-porous) surfaces.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention claimed is:

1. A copolymer that is the product of ring-opening metathesis polymerization of monomers comprising an azidoaryl-substituted cyclooctene having the structure

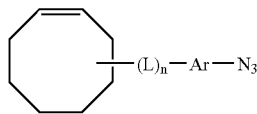

wherein n is 0 or 1; wherein L is selected from the group consisting of —O—, —N(R$^1$)C(=O)—, —C(=O)N(R$^1$)—, —N(R$^1$)S(=O)$_2$—, and —S(=O)$_2$N(R$^1$)—, wherein R$^1$ is hydrogen or C$_1$-C$_6$ hydrocarbyl; and wherein Ar is a C$_6$-C$_{18}$ arylene group.

2. The copolymer of claim 1, wherein n is 1, L is —N(H)C(=O)—, and wherein Ar is 1,3-phenylene or 1,4-phenylene.

3. The copolymer of claim 1, wherein the azidoaryl-substituted cyclooctene is 4-azido-N-4-cyclooctene-1-yl-benzamide.

4. The copolymer of claim 1, wherein the monomers further comprise cyclooctene.

5. The copolymer of claim 1, wherein the monomers further comprise alpha-4-cycloocten-1-yl-omega-hydroxy-poly (oxy-1,2-ethanediyl).

6. The copolymer of claim 1, wherein the monomers further comprise a phosphorylcholine-substituted cyclooctene having the structure

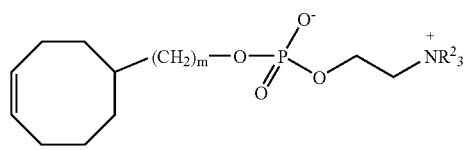

wherein m is 0 or 1, and each occurrence of R$^2$ is independently C$_1$-C$_6$ alkyl.

7. The copolymer of claim 6, wherein each occurrence of R$^2$ is methyl.

8. The copolymer of claim 1, wherein the monomers further comprise cyclooctene and alpha-4-cycloocten-1-yl-omega-hydroxy-poly(oxy-1,2-ethanediyl).

9. A copolymer that is the product of ring-opening metathesis polymerization of monomers comprising 4-azido-N-4-cycloocten-1-yl-benzamide.

10. The copolymer of claim 9, wherein the monomers further comprise cyclooctene.

11. The copolymer of claim 9, wherein the monomers further comprise an alpha-4-cycloocten-1-yl-omega-hydroxy-poly(oxy-1,2-ethanediyl).

12. The copolymer of claim 9, wherein the monomers further comprise cyclooctene and an alpha-4-cycloocten-1-yl-omega-hydroxy-poly(oxy-1,2-ethanediyl).

13. The copolymer of claim 12, wherein the alpha-4-cycloocten-1-yl-omega-hydroxy-poly(oxy-1,2-ethanediyl) comprises about 10 to about 500 oxy-1,2-ethanediyl units.

14. The copolymer of claim 12, comprising about 70 to about 90 weight percent of oxy-1,2-ethanediyl units, based on the total weight of the copolymer.

15. The copolymer of claim 12, wherein the monomers comprise about 10 to about 30 weight percent of 4-azido-N-4-cycloocten-1-yl-benzamide, about 50 to about 70 weight percent of cyclooctene, and about 10 to about 30 weight percent of the alpha-4-cycloocten-1-yl-omega-hydroxy-poly (oxy-1,2-ethanediyl).

16. The copolymer of claim 9, wherein the monomers further comprise a phosphorylcholine-substituted cyclooctene having the structure

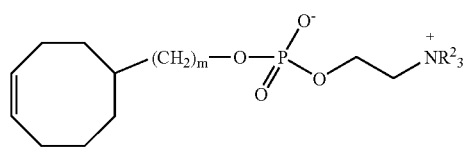

wherein m is 0 or 1, and each occurrence of R$^2$ is independently C$_1$-C$_6$ alkyl.

* * * * *

UNITED STATES PATENT AND TRADEMARK OFFICE
CERTIFICATE OF CORRECTION

PATENT NO. : 7,750,103 B2  Page 1 of 1
APPLICATION NO. : 11/899869
DATED : July 6, 2010
INVENTOR(S) : Todd S. Emrick et al.

It is certified that error appears in the above-identified patent and that said Letters Patent is hereby corrected as shown below:

Title Page,
Item (73), Assignee, delete "Board of Regents, The University of Texas System, Austin, TX (US)".

Signed and Sealed this
Nineteenth Day of July, 2011

David J. Kappos
*Director of the United States Patent and Trademark Office*